(12) United States Patent
Belas et al.

(10) Patent No.: US 8,058,417 B2
(45) Date of Patent: Nov. 15, 2011

(54) BIOSYNTHETIC PATHWAY AND GENES REQUIRED FOR TROPODITHIETIC ACID BIOSYNTHESIS IN SILICIBACTER TM1040

(76) Inventors: Robert Belas, Catonsville, MD (US); Haifeng Geng, Baltimore, MD (US); Ryan Powell, Baltimore, MD (US)

( * ) Notice: Subject to any disclaimer, the term of this patent is extended or adjusted under 35 U.S.C. 154(b) by 0 days.

(21) Appl. No.: 12/472,296

(22) Filed: May 26, 2009

(65) Prior Publication Data

US 2010/0035960 A1    Feb. 11, 2010

Related U.S. Application Data

(63) Continuation-in-part of application No. PCT/US2007/085681, filed on Nov. 27, 2007.

(60) Provisional application No. 60/861,117, filed on Nov. 27, 2006, provisional application No. 61/174,841, filed on May 1, 2009.

(51) Int. Cl.
| | |
|---|---|
| *C12N 9/02* | (2006.01) |
| *C12N 9/10* | (2006.01) |
| *C12N 9/16* | (2006.01) |
| *C12N 15/31* | (2006.01) |
| *C12N 15/53* | (2006.01) |
| *C12N 15/54* | (2006.01) |
| *C12N 15/55* | (2006.01) |

(52) U.S. Cl. ...... 536/23.2; 536/23.7; 435/189; 435/193; 435/196

(58) Field of Classification Search ........................ None
See application file for complete search history.

(56) References Cited

U.S. PATENT DOCUMENTS

| 2004/0175407 A1 | 9/2004 | MacDaniel |
| 2006/0257961 A1 | 11/2006 | Apicella et al. |
| 2009/0142429 A1 | 6/2009 | Belas et al. |

FOREIGN PATENT DOCUMENTS

WO    2006127823 A2    11/2006

OTHER PUBLICATIONS

Belas, R., et al., Mar. 13, 2007, GenEmbl Accession No. EF139204, "Mutant Silicibacter sp. TM1040 Acyl-CoA dehydrogenase (tdaE) gene, complete sequence", Length = 1701nt.*
Belas, R., et al., Mar. 13, 2007, GenEmbl Accession No. EF139205, "Mutant Silicibacter sp. TM1040 phosphopantothenoylcysteine decarboxylase (tdaF) gene, complete sequence", Length = 672nt.*
Miller, Todd R., et al., "Chemotaxis of Silibacter sp. Strain TM1040 toward Dinoflagellate Products", "Appl. Environ. Microbiol.", Aug. 2004, pp. 4692-4701, vol. 70, No. 8.

(Continued)

*Primary Examiner* — Manjunath Rao
*Assistant Examiner* — William W Moore
(74) *Attorney, Agent, or Firm* — Steven J. Hultquist; Kelly K. Reynolds

(57) ABSTRACT

Production and use of a sulfur-containing compound, tropodithietic acid (TDA), from the *roseobacter Silicibacter* sp. TM1040 is described. Specifically, a biosynthetic and regulatory pathway for TDA biosynthesis in *roseobacters* is described. The TDA produced from *roseobacters*, specifically *Silicibacter* sp. TM1040, is shown to have antibacterial activity, in particular against *Vibrio anguillarium, Vibrio cholerae, Vibrio coralliilyticus, Vibrio shiloi, Halomonas* spp., *Mycobacterium marinum, Mycobacterium tuberculosis, Pseudomonas elongate, Spongiobacter nikelotolerans*, and *Staphylococcus aureus* (MRSA).

2 Claims, 10 Drawing Sheets

OTHER PUBLICATIONS

Bourne, David G., et al., "Diversity of bacteria associated with the coral Pocillopora damicornis from the Great Barrier Reef", "Environ. Microbiol.", Aug. 2005, pp. 1162-1174, vol. 7, No. 8.

Brinkhoff, Thorsten, et al., "Antibiotic Production by a Roseobacter Clade-Affiliated Species from the German Wadden Sea and Its Antagonistic Effects", "Appl. Environ. Microbiol.", Apr. 2004, pp. 2560-2565, vol. 70, No. 4.

Bruhn, Jesper Bartholin, et al., "Ecology, Inhibitory Activity, and Morphogenesis of a Marine Antagonistic Bacterium Belonging to the Roseobacter Clade", "Appl. Environ. Microbiol.", Nov. 2005, pp. 7263-7270, vol. 71, No. 11.

Christie, Peter J., et al., "Bacterial type IV secretion: conjugation systems adapted to deliver effector molecules to host cells", "Trends Microbiol.", Aug. 2000, pp. 354-360, vol. 8, No. 8.

Miller, Todd R., et al., "Dimethylsulfoniopropionate Metabolism by Pfiesteria-Associated Roseobacter spp.", "Appl. Environ. Microbiol.", Jun. 2004, pp. 3383-3391, vol. 70, No. 6.

Ruiz-Ponte, C., et al., "The Benefit of a Roseobacter Species on the Survival of Scallop Larvae", "Mar. Biotechnol.", Jan. 1999, pp. 52-59, vol. 1, No. 1.

Chen, Feng, et al., "Induction of Multiple Prophages from a Marine Bacterium: a Genomic Approach", "Applied and Environmental Microbiology", 2006, pp. 4995-5001, vol. 72, No. 7.

Galperin, Michael Y., "Sampling of microbial diversity by complete genomes", "Environmental Microbiology", 2006, pp. 1313-1317, vol. 8, No. 8.

Moran, Mary Ann, et al., "Genome sequence of Silicibacter pomeroyi reveals adaptations to the marine environment", "Nature", 2004, pp. 910-913, vol. 432, No. 7019.

Moran, M.A., et al., "Ecological Genomics of Marine Roseobacters", "Applied and Environmental Microbiology", 2007, pp. 4559-4569, vol. 73, No. 14.

\* cited by examiner

| strain | SO$_4$ | SO$_3$ | Met | Cys | DMSP |
|---|---|---|---|---|---|
| *cysI* growth | - | - | - | + | - |
| WT growth | + | + | + | + | + |
| *cysI* TDA | - | - | - | + | - |
| WT TDA | + | + | + | + | - |

SEQUENCE LISTING

<160> NUMBER OF SEQ ID NOS: 10

<210> SEQ ID NO 1
<211> LENGTH: 24
<212> TYPE: DNA
<213> ORGANISM: Unknown
<220> FEATURE:
<223> OTHER INFORMATION: primer

<400> SEQUENCE: 1
cagatgatgg tgccaaagga ctat                                    24

<210> SEQ ID NO 2
<211> LENGTH: 25
<212> TYPE: DNA
<213> ORGANISM: Unknown
<220> FEATURE:
<223> OTHER INFORMATION: primer

<400> SEQUENCE: 2
ggtcagtttc ttctgcacat actgg                                   25

<210> SEQ ID NO 3
<211> LENGTH: 21
<212> TYPE: DNA
<213> ORGANISM: Unknown
<220> FEATURE:
<223> OTHER INFORMATION: primer

<400> SEQUENCE: 3
ttgcagtatc caatggtcgt g                                       21

<210> SEQ ID NO 4
<211> LENGTH: 21
<212> TYPE: DNA
<213> ORGANISM: Unknown
<220> FEATURE:
<223> OTHER INFORMATION: primer

<400> SEQUENCE: 4
tgaattgcgt cagagtttgc c                                       21

<210> SEQ ID NO 5
<211> LENGTH: 20
<212> TYPE: DNA
<213> ORGANISM: Unknown
<220> FEATURE:
<223> OTHER INFORMATION: primer

<400> SEQUENCE: 5
cgctttccgg aactggagat                                         20

<210> SEQ ID NO 6
<211> LENGTH: 21
<212> TYPE: DNA
<213> ORGANISM: Unknown
<220> FEATURE:
<223> OTHER INFORMATION: primer

<400> SEQUENCE: 6
ggctgccgta tagtttcagc a                                       21

<210> SEQ ID NO 7
<211> LENGTH: 5844
<212> TYPE: DNA

<213> ORGANISM: Silicibacter sp. TM1040

<400> SEQUENCE: 7

```
gcccccggg ggggggcccg ggccaggtaa attcgcccgg ggttttacgg gggggttttt      60
tttcccgaaa ggatgacgca aaattccacc cagtttcctg gccccggaaa tagaagcccc    120
ccggttcggg gggtgaactc ggggggaggg ggcctttgcc catcccagat gcagcttgcg    180
cagataggcc gtcggttgac cccccaagag ccaagccgcc tcgccgggag gtgaacttgc    240
gctccccttg gcgctcgggg ggaaaggagg ctttcgcgtt gattgtgcaa tgtgcgccca    300
gccattcgaa atgctcccga ataagctggt tgagatcctc atgcagcgct tctgctgctg    360
ccggagcctt ggtcgttgca tgccgtcctg cccttcgtat cctctgtgac ggttccactg    420
tgacggtggc gatggcgcaa ggagccgcct cagatcgggc gttttctctt cagcctgccc    480
gccgtgttca cggaaatcga cgttttttgta tctttccgtg actatttacc gccgagcggg    540
attcgtgcaa gggttttctg cccaagttat ccacaggatg cgcaattttt gagccccgca    600
gacgcggtga tggcctctgg gggcggagaa gttgcctgtc atacccgtga cacgagacta    660
aaggcattct gcaatagcca gccgcccagt ccggtctctc tgtgaccttt ggcatccggg    720
acggcgccgc caaaccggcc ccatgtcagc gccgcattgc gggaaacgcc agggcgcaga    780
agacccgaag acggcccgca aaccgccgga tgccgcgtgg acaggggcg ggacaggatg     840
gagaaccgtg gtggcctcgc cctttctggc gagggatttt cgcgcgtaac ccgtgtggcg    900
aaacccccgcc gaagcgcgta agtctcagaa aaaatgacta aattatcggc ttgataaaat    960
ctgtagacga cataacctat aggagattcg tttgccagtg tttttaccctt ggttgttgag   1020
ggcacattaa taagaccgcg gttccggcca gctattgacc gccgccgttg cagaccccct   1080
gcaatgcgcg ccgtccagcg agagagaccg actttcccaa aacccaaccc aagaccagat   1140
atggtgcact gtgcgtcatc agtgagtggg agcgagatta gatttggaca ttcaacagct   1200
aagagtcttt gtcaccgttg caaaacatgg cagcatcacc cgtgcttctg acattctgtg   1260
gcagccagcc ctcggtgagc gcgcagatca agagcctgga gacgacactc gggatcacgc   1320
tgtttgagcg caccctcgcg gcatggtgg tcacgcaggg gggcgagcgc cttctggatg    1380
aggcgaccgc ttgtggatcg gcacaaacag ttcatgcagg aggcctcgcg actgaagggc   1440
agtgtctcgg ggctgtttgc catgggcgca gggcggcatt cgggcaacgg ctttgtcagc   1500
tctttcctgc attgtctcgg aacgctttcc ggaactggag atcgagctca acacctggc    1560
ctcggcgcag gtgatcgagg ggctgcgcga tcagtcgctg acatgggat ttttcaccga    1620
aaccgaaagc gacacctcga ttgacgctgg tggaggtggc cagtttcggc atctaccttg   1680
cggcgccgcg cgggatgatc cgttgttcag agacccctga ctgggcgcgt cttcaggatc   1740
agatctggat tgtctcgtct catgtggcgc tgcggtcgct gggccaatgc cctcatggag   1800
cagcatgaca ttcgcccaag gcgggtgatc aaggttgatg acgaggcggt gacgcggacg   1860
ctggtggcaa gcggagccgg ggtcgggctg tgcattctcg ggtgatgaag cgctgacgcc   1920
gcccgatgac atcgacctgt tgcaccgggt gcgcaagacc cgcgcgatca tgtgcggcta   1980
tctcgaagcg cgcagcgatg atccctctat tcgcgcgtag ataattggtt ctggattggc   2040
tgaaatctca acaaaaggc gaaacaccct ccttgttgca attggcgtaa tcacaatttc   2100
atttgagaat ccccaaataa gggaatacgt cattcgagag tgttatttg gagttgtcat    2160
gattacgatt tatagcctct gtggcaaaga cgatattcat tattcccgc atgtttggaa   2220
agtcattatg gccctgcatc acaaagggct ttcatttgac gtggtgccgt ggattttcga   2280
```

```
cgatccgcga catcgagggc ggggcgttca acagcgtgcc ggtgctgcgc gatggcgacc    2340
gggtgatcgg ggacagcttc gagatctgca cctatctgga tgccgcctac ccggtgcccc    2400
ggcctgtttg ccggtgcggg cagtgaggcg caggtgcggt tcctggaaag ctattgcctg    2460
acggcgctgc acccaccgct cgcggtgatc gcggtgatgg cgatgcatga catcatgcat    2520
cgggcgatca gcctatttcc gggccaaacg cgaagagcgt tttggcgtgt ccatcgaggc    2580
gctggcggaa accgcgcccg ccgagcgcgc gcgattgcag gagcggctgg cgccggtgcg    2640
cgccgtctta cgcatcacac tggcttgcgg gcgatgcccc ggcgatggcc gattacgtgg    2700
tgttcagcgc cttgcagtgg tgctgggtcg tggggctgcg cgatcttctg tcccccgacg    2760
attcggtggc gcgtggttca gccgtgtcag gccctgtttg gaggggcggc gcaaaagcct    2820
gctggagccc cgcgctaagc ctgagctgaa tctgcgcgaa caaaccggca aaacccggcc    2880
caaattcatc tgatgcgccc ccgatcgggg ccgcttttg ttggttttgg ggcatttacg     2940
gctgtgtcac caaagccgat agctgacctc agttttttccg aattgcgaca aagcgcgtca    3000
ttggatcata tgagtcccaa ggttcgatac gtcctgagcg aattgatttt tgaaacggtt    3060
ggaaatgaac aagtaaatgg ttgcgtatcc gaaattgaat ttcagtcaat tgatgatgcc    3120
attggaggac tcttgaatgg acgtcgcgct atggacggtc ccagaaccaa cgcagtgaag    3180
acatatccaa aacctatgac tggggtgcgc catgttcata ccctgggacc ggctggcacc    3240
aactgtgaaa aggcggcgct gaaatgggcg cgctcagtg ccgcaatgct gcctggtcct      3300
gcatgactcg atggaggagg ccgcagagca ggtcgcggcc tgcggctgtt cggtgcttct    3360
gagcgtggtg gcctacccgc agctgcattc gatcatctac gacatatcgc gcatctgggc    3420
ttctggatgt gttcatcatg aagaccgacg acatggtgct ggcctcggtg agcggcgcca    3480
tgccgacgct gtgccagacc cacccggcgc cggaaaagct gctgccgccc gagatgcagc    3540
ggatctatgc gacgagcaat tcccacgcgg cctctgaggt ggcggcaggg cggggcgatg    3600
gctgcatcac cacgcgtgcc gccgccgaag cacgggcttt tggtggtgca gacctttggc    3660
caggtgccga tggggttcac cattcacggc ccgctcaagc atgcgggctg cgcggacacc    3720
gcctttgacg tttcagcacc agatcacaac aggattttcc caatgaccca acgcgcattt    3780
gagacccgga tcgaagtccg ctaccgcgac accgactcga tgggccatat cagcagcccg    3840
atctactacg actacatgca gtcggcctat ctggaataca ccgcgcgctgc tggagctgcc    3900 gaagtccgaa aagctgccgc atatcatggt gaaaaccgcc tgcgagtaca tcagccaggc    3960
ctattacggc gataccgtgg tggtgctgag caaagtgtcg aaattcgcgc aagagtttcg    4020
agatcgacca tgagatccgc cttggcagcg cggacggccg ggtggtggca agctacagt     4080 cggtgcatgt gatgttcgat tacgaaaagc agagcaccta cccggttccg agatttcgc     4140 agccgcgtcg ccgatttca ggacgccgcc tgagcgcgcg ccacggtcca gagagggaga     4200
atgcaatgga tttgagttgg agcacgcagc agcagtcgat ccgggcggag tttgcctcct    4260
cggagccgca cagaccgcga tgagctgcgt cttggacggc gcgcctttga ccagcagacc    4320
tgggatcagc tgggagaggc gggcctgtgg cagatgatgg tgccaaagga ctatggtggc    4380
accggggcgg accggggctt gctggtggga tgtcaccgcc gcccttgagg ggctggcctc    4440
gaccatccgc gcgccgggc tgttgctgtc ggtgatcgcc caagcgggta tggcctacgc     4500
gctggagctc ttggcacccg gcgcagaaat ccgactattt ccgccgcatc ctgcgcggcg    4560
cgctgagcgc cacggccatc gcggacccccg acaccggcac cgatgtccgc gccagctcca    4620
cttacctcag cccgcgccga acgaacctttt gtgctcaacg ggaagaaata caacatcgcc    4680
```

-continued

| | |
|---|---|
| catgcgccgg tggcgaattt cactctggtg gtctgcaagc tcgaaggcca tgcccgcgac | 4740 |
| ggcatctccc tggttctggt ggtcaggaca gaagggcgtc accatcggtg ccaaggatcg | 4800 |
| caagcttgga aacctagatt tgccgacggg ggcgctctcg tttgagaatg tgccgctgca | 4860 |
| ctatgggcat attctggggg tgccgggcaa gggctgcgaa ccttgtgcgg tttgtctcgc | 4920 |
| tggggcggat ctattacggg ctggtggcgg cgaccctgtg cggcccgatg cttgcggagg | 4980 |
| cgctgtctta tgccaaggcc cggcagacct ttggcagccc atcgtgatca ccagtatgtg | 5040 |
| cagaagaaac tgaccgatat gcgcatcgcg gcagagaccg ccaaatggac tcttatggg | 5100 |
| gcgttgcacc agttgctgag cggcgcgccc gaggcggtga gagctgttcg atgccaagct | 5160 |
| ggccggagcc agcgcgatca ccgatggggc cgtggacctg ctgaaactat acggcagccg | 5220 |
| gggctatcac gtagggcgag gtgtccacgt tcctgcgcga tgcgctgcct tttgcagcgt | 5280 |
| ggcggcaccg aggaaatgca tcggcgcaac atcatgaacc agatgatgcg agaggcccgc | 5340 |
| ccggccaagt ccaagcccgc cgccccggcg cgggatctgg aaaccgtctg aggccgcctt | 5400 |
| tattgattgg agacaatcat gttaaaagat ttcaacagct tgcgctgtct cgcgcatggt | 5460 |
| gctgcactag cgctgtact gggcgcgatg ccgcttgcgg cgggtgccgc agaagaggga | 5520 |
| tcctgagcga ggccagatcg actgggccgc cgcagaggac tcggcggtgg caaccgctac | 5580 |
| agcagaagcc gcactcacgg aggcgtttct ggccctgccc cgcgagcgcc g agcccaccgg | 5640 |
| tttgcggtga tgctctttgg gcggcggcgg atctgcccga gccgggcttt gtcagtcagg | 5700 |
| gcagcgccta tgtggcctat tacgcgcagg acgatattca gctttcgatc tcggggtcaa | 5760 |
| aggcggtggt caggcggggg atgcgctgtt ctgcaccatg ccccaagcgc gtgggaaagc | 5820 |
| atcggaacgg gcgcggatta caat | 5844 |

<210> SEQ ID NO 8
<211> LENGTH: 2501
<212> TYPE: DNA
<213> ORGANISM: Silicibacter sp. TM1040

<400> SEQUENCE: 8

| | |
|---|---|
| gcgccggtgg agagaacaaa catcctcgcg gcttgctgga gttctacctc gaggaagcga | 60 |
| gatcacggcc cgccacctgc tgacacaagt ctcggtatct gagtcgaagg tgtgccggtg | 120 |
| cgcgagggaa caccgttc gcaaaccgct ctcccggctc agggtggggg atcacctgcg | 180 |
| cagcgccgac cgcatcgtgc ggccgaggac gtcgaagcct ttggccacct cacgggcgat | 240 |
| ctgttttatg cccttggacg aggccgccgc gcgcaatcat ccgttctttg acgggcgcgt | 300 |
| cgcgcatggg caatacatca tggcgctggc caacggcctc tttgtggacc ccgagcccgg | 360 |
| ccccgtgctg gccaatctcg ccccgcgatc tgcgtttttt tgcgccggtc tatttcgaca | 420 |
| ccgcgctcta tgtgacgctc acctgctgct gcatcggccc cctcaacagg tcgggcgcgg | 480 |
| ccgaagtgca atggagctgc aggtcgggc agcgatgacg acacccgcgt ggcccagttc | 540 |
| gacctgctga cccttgtcgc cgcccaatgg ccgccccagc ccgcccccg cgcctgagag | 600 |
| gcccgagagg cctgagacgc cgggtacgcc aatgccccct tcccctgctat tgaaacaaaa | 660 |
| ggattccaa tgacctctgc tccaaagccc cgcatcctga tcggtgcctg cggctcgctc | 720 |
| gacctgctga tgctgccgca gcacctgcgc gccatcagga cacatcgact gcacgctgag | 780 |
| cctgatgctc acgccgacgg cggtgaaatt tgtcaacacg gatgcgctgg ccctgctggt | 840 |
| ggaccggctg atcacggcg accgcccgga cgactggcca cgcacaagcc ggacgccttg | 900 |
| ccgccgatca cgatcttctt gcggtgctgc cgacaaccgc aaacaccctc agtgccgtgg | 960 |

```
ccaacggcag ctcgcagaac cgcctcacca cggtgatcct cgcagcggat ttccggactg   1020
ttctttcccg tgatgggcgg gccgatgtgg gacaaggcct cggtgcagcg caatgtgagc   1080
cagatccgcg ccgacgggta tgaggtgttt cagccggtct ggcgcgaaca cagcgcccgc   1140
atcgcaaaag gtccacggcc atcattcgct gccggacccc gcggatgtgg tcgacatcct   1200
ccaaagccgc ctgcccgcgc agcgctgacc cggcctaccc gcctgccccc cctgcccac    1260 agatctgtcc aaacaggaaa cgccgccgga tctcctccgg cggcgtttct cgtggtctct   1320
ttgcctttgg ccctagccgg tcacatcacg caggccgggg cgcagcatgg ccacagccg    1380 cgcctgccca gcgccgcaga tagagcccca ccccaaagga gagatgcgtc atcgcgctct   1440
tcagctgcgc aaaggtcgga tcgggcttgt tgctggccat gatgcccgca cccatcgccg   1500
gctgcatcac aaaaagggaa agacatggtg ccgagcccca ccacaagcgc cagcaacacc   1560
tgcggccgtt gcagctgccc gacgcccccg atcgccacaa agagcgccgc aaagaccacg   1620
cccaccgcat aatgtaccgc cagccaagcg cgcctcaccc gccaccggcg ccgccgcgcg   1680
aatgctctca tgggcgaaca cgccctcggg catatggccg acccaacgcc ccaccagggc   1740
aaagttgctc tgcggaatcg caaacagcgc ctccgccagc acggcccaga gatccatcac   1800
caccgtggca cccacgccca agcagtacgc gaaaaacaat ctgtgcagga gacatcctga   1860
gaaccctctc tctcgctcac aggcgccagc cgcctggcca gcccctttg aagatgcgcc    1920 cgacccatca aaatgcgggc cggcggtac gcgttacgcc ctttactggg acaccatcgt    1980
gctatcgaac ccggcacagg tctggggcgc ggcggcctcg cgcgctgaggg gttgtagcgc  2040 ggttgcagcg acgtgatgcc cgatctggta gccacatatc gcccaccgcg ttcgagcgcc   2100
ggtaatgcac gccgccaatc aggcgcgatt ccgattcctc ttcggcgagg tgctgcagac   2160
tgtcgtaaga cttgctgatg ttggcggccc cctcaaaggg acgggaaagg cgcgctgcca   2220
aagaccgagg tcatcacctc aagcgctgcg ctgccgctgg tgcaatgctg acaggggtat   2280
tcgggatgca tcggcgcagg aatgcgcgat tcccagacca gaccggctca ggtcggggtg   2340
gttgtaggtt ttgcccaacg cctccacggc ggtctgtggc cgccagagcg cgtagctgta   2400
cttggcgttg aacccggcca ccaacgcatc gctcagggca acattcaaca cgccacatgc   2460
gcgtttcctc gagaagaggc agcgcgccag ccgcgcagag g                      2501
```

<210> SEQ ID NO 9
<211> LENGTH: 934
<212> TYPE: DNA
<213> ORGANISM: Silicibacter sp. TM1040

<400> SEQUENCE: 9

```
gaattcgccc gccttgatcg cggcgcgcac ctcttccatc ggggcgatgg cctcttcggg    60
caccatcgac gcggtaaagg agatgtcgtt gccgccctct ttcatgaggc caaagcgggt   120
gtagtccccc gctggaattg cccgccgcgc gatccgccag cgccgcccca aggatggggc   180
caaagttcca gatcgcattc gagaacacgg tctcggggta gcgctcggta taatcggtga   240
gcgagcccac cgctgatgcc gcgttccttg gcggcgtcgg cggtgccgat ccgctcgcca   300 agaggatgt cggcgccgga atcgatctgc gccagaccgg cctcgcgggc cttgggcgga   360
tcaaagaagg tgccgataag tgatgagatg ggtcgcatcg ggacgcaccg cgtcgacacc   420
ctgacggaac ccgttgatga gcatgttgac ctcggggatc gggatcgccc ccaccgcgcc   480
aaagacgccg gactggctca tcttgccgca gcatgccgca cagataggcc gcctcgtggt   540
tccaggtgcc aaaggtgcca agttgtcgc ccgcgggctt gccgctggag cccatcacga    600
```

```
agcgcgtgtc gggatagtcg cccgccacct gcgcgctcgc gctccaccgc ataggcttcg    660
cccacgatca catccgcgcc ctgctcggca tattcacgca tcgcgcgcgc atagtcggtg    720
cccgcgatcc cctcggaaaa gacatattcg atctcgcgcg cttgccgctt cgagcatcgc    780
cacatgcaga cgcgagttcc acgcgttctc caccggcgag gcatgcaccc ctgccacctt    840
gatcggcgct tgcgccagca ccatcggcgc cggcagcaac gaggccgccc caagtgctgc    900
gccgctcttc aggatcgatc ttcgggttca tacc                                934

<210> SEQ ID NO 10
<211> LENGTH: 687
<212> TYPE: DNA
<213> ORGANISM: Silicibacter sp. TM1040

<400> SEQUENCE: 10
gaattcctcg gcgcggacat cctctgccag catttcgatc tcttgcgcac gcagccgcag     60
gggagagaga tcaaagccat aggcgacctt ctcggtgcca tagcgccgcg catagcgttt    120
gccattggct gtcgcgtctg agcagcaaac cggcctcgac caggcgggcg agatagcggc    180
gcatggtgga attggccatg ccgttgagcc gctcgcagat gctctggttc gagggtgaa     240 tgacaaggtc gcgtcacggg cagctcggcc ccggaccaga agctcaagag cgcttgcagc    300
actgagagat cccggtcgct gaggccaaaa tgatgccggg cggtcgcgag atcgcgcagc    360
acattccact tgctgacagt gaagtgcggt cgtgggctga gacctcgggg cctcgggatc    420
ggtggatgcg gcaggcatac gggagctggc cgcctgaagc tgcgtctgac gtttgatcag    480
aacagcatca acggtgcgcc caaaagcgga caggatgata ccccatgttt cattcacgaa    540
gacaaagaaa tcccgttctg cgaatcacat ttgacttgca gtttcaggct cctgacacta    600
gcttgatggt gctaaacaca agtcagggtc tgtgggcgat gtctttgcgg gaccttttct    660
tttgtctgct cgtgcctcct ttcttag                                        687
```

US 8,058,417 B2

BIOSYNTHETIC PATHWAY AND GENES REQUIRED FOR TROPODITHIETIC ACID BIOSYNTHESIS IN SILICIBACTER TM1040

CROSS-REFERENCE TO RELATED APPLICATION

The present application is a continuation-in-part under 35 U.S.C. §120 of PCT Application No. PCT/US07/85681, filed Nov. 27, 2007 in the names of Robert Belas and Haifeng Geng and published on Jun. 5, 2008 as PCT Publication No. 2008/067338.

This application also claims the benefit of priority under 35 U.S.C. §119 of PCT Application No. PCT/US07/85681 as referenced above, U.S. Provisional Patent Application No. 60/861,117 filed Nov. 27, 2006 in the names of Robert Belas and Haifeng Geng and U.S. Provisional Patent Application No. 61/174,841 filed May 1, 2009, in the names of Robert Belas, Haifeng Geng and Ryan Powell. The disclosures of these references are hereby incorporated by reference in their entirety, for all purposes.

GOVERNMENT RIGHTS IN INVENTION

Work related to the invention was conducted in the performance of National Science Foundation Grant MCB0446001. The United States Government has certain rights in the invention.

FIELD OF THE INVENTION

The present invention relates generally to *Roseobacter* bacteria and the production of antibiotic tropodithietic acid (TDA) by use of such microbial species. The invention also relates to use of the TDA in the treatment or prevention of bacterial disease.

BACKGROUND OF THE INVENTION

Bacteria of the *Roseobacter* clade of marine alpha-Proteobacteria stand out as some of the most critical players in the oceanic sulfur cycle due to the ability of several genera to degrade dimethylsulfoniopropionate (DMSP). While *roseobacters* are wide-spread throughout the marine ecosystem, their abundance is significantly correlated with DMSP-producing algae, especially prymnesiophytes and dinoflagellates, such as *Prorocentrum, Alexandrium* and *Pfiesteria* species.

*Roseobacters* have abundant and diverse transporters, complex regulatory systems, multiple pathways for acquiring carbon and energy in seawater, and the potential to produce secondary, biologically active metabolites.

SUMMARY OF THE INVENTION

The present invention relates to *Roseobacter* bacteria and to the production of antibiotic tropodithietic acid (TDA) by use of such microbial species.

In one aspect, the invention relates to an isolated nucleic acid encoding a megaplasmid (pSTM3) of *Silicibacter* sp. TM1040, wherein the nucleic acid comprises genes involved in tropodithietic acid biosynthesis of *Roseobacter* bacteria.

Another aspect of the invention relates to a protein encoded by a nucleic acid sequence comprising any of SEQ ID NO: 1, SEQ ID NO: 2, SEQ ID NO: 3, and SEQ ID NO: 4, wherein the protein is involved in the biosynthesis of tropodithietic acid by *Roseobacter* bacteria.

Yet another aspect of the invention relates to an antibacterial composition comprising tropodithietic acid isolated from bacteria of the *Roseobacter* clade.

A further aspect of the invention relates to a method of treating or preventing bacterial disease or infection in a subject in need of such treatment or prevention, comprising administering to said subject an antibacterial composition comprising tropodithietic acid isolated from bacteria of the *Roseobacter* clade, wherein administration of the antibacterial composition is effective in killing the bacteria causing the bacterial disease or infection. In one aspect the disease or infection is caused by any of *Vibrio anguillarium, Vibrio cholerae, Vibrio coralliilyticus, Vibrio shiloi, Halomonas* spp., *Mycobacterium marinum, Mycobacterium tuberculosis, Pseudomonas elongate, Spongiobacter nikelotolerans,* and *Staphylococcus aureus* (MRSA).

In another aspect the invention provides a method of treating or preventing *Mycobacterium tuberculosis* or *Staphylococcus aureus* (MRSA) disease or infection in a subject, comprising administering to said subject an antibacterial composition comprising tropodithietic acid, wherein the antibacterial composition is effective to kill the *Mycobacterium tuberculosis* or *Staphylococcus aureus* (MRSA) causing the disease or infection.

In still another aspect, the invention provides a bactericidal method, comprising contacting a surface or object containing *Mycobacterium tuberculosis* or *Staphylococcus aureus* (MRSA) with tropodithietic acid, wherein the tropodithietic acid is effective to kill the *Mycobacterium tuberculosis* or *Staphylococcus aureus* (MRSA) on the surface or object.

Another aspect of the invention relates to a method for producing an antibacterial composition comprising tropodithietic acid, the method comprising:
  a) culturing *Silicibacter* sp. TM1040 in a culture medium supporting growth of the bacterium and production of tropodithietic acid; and
  b) recovering the tropodithietic acid,
  wherein the recovering comprises:
    i) separating the tropodithietic acid from the culture medium; and
    ii) purifying the tropodithietic acid by high performance liquid chromatography.

Yet another aspect of the invention relates to a plasmid pSTM3.

Another aspect of the invention relates to a compound selected from the group consisting of:
  1,2-dihydro-phenylacetyl-CoA;
  2-hydroxy-7-oxo-cyclohepta-3,5-dienecarboxylic acid;
  2,7-dihydroxy-cyclohepta-1,3,5-trienecarboxylic acid;
  2,7-dihydroxy-3-oxo-cyclohepta-1,4,6-trienecarboxylic acid;
  2,7-dihydroxy-3-thioxo-cyclohepta-1,4,6-trienecarboxylic acid; and
  7-hydroxy-2-mercapto-3-thioxo-cyclohepta-1,4,6-trienecarboxylic acid.

Other aspects, features and advantages of the invention will be more fully apparent from the ensuing disclosure and appended claims.

Insets show the UV spectra of the HPLC peak corresponding to the antibiotic activity. For 27-4, the peak is TDA.

Figure 3:
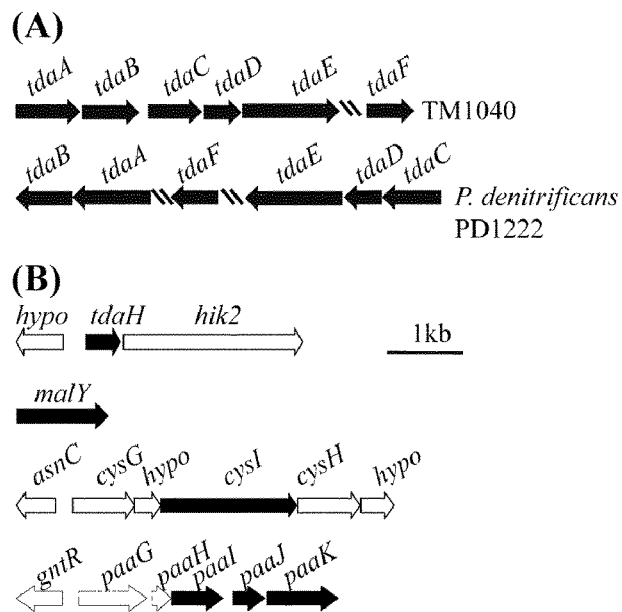

FIG. 3 provides maps of the genes required for synthesis of TDA in TM1040. The black boxes indicate the ORF interrupted by the transposon. Arrows indicate ORFs transcriptional orientations and hatch marks indicate a break in the region.

Figure 4:
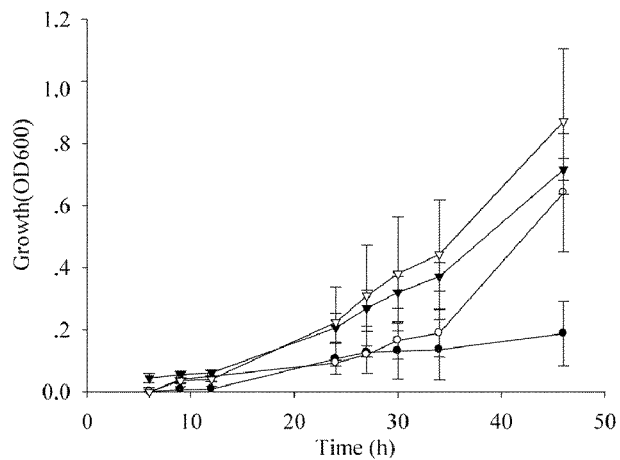

FIG. 4 provides the results of experiments showing that growth and TDA synthesis is affected by mutations in cysI.

Figure 5:
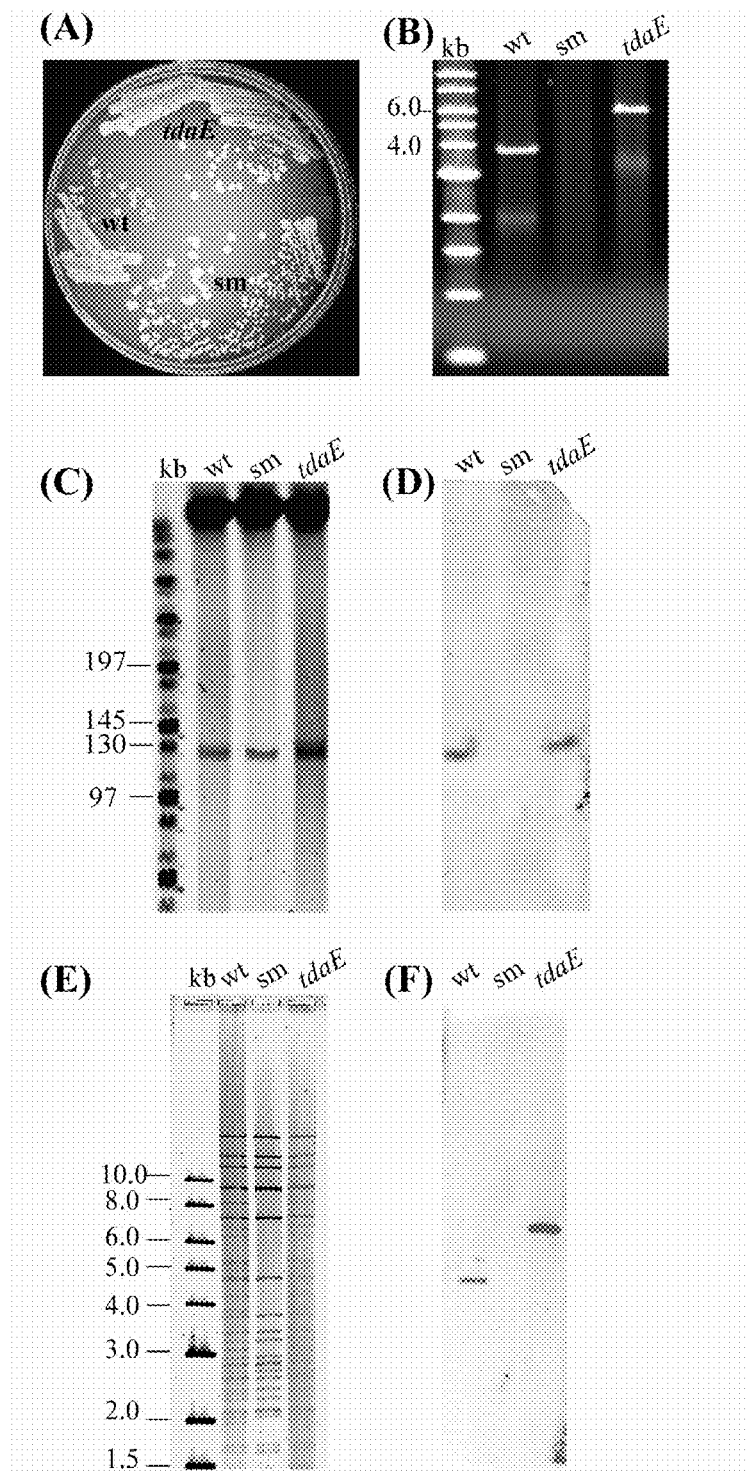

FIG. 5 provides the results of characterization studies of TM1040 (wt), tdaE:Tn mutant (strain HG1265) and a spontaneous mutant (sm; TM1040SM), where FIG. 5A provides pigment analysis, FIG. 5B provides PCR amplification results, FIG. 5C provides PFGE separation of total DNA, FIG. 5D provides a Southern blot, FIG. 5E provides NcoI digestion of plasmid DNA and FIG. 5F provides Southern blot hybridization of NcoI-digested plasmid DNA to tdaE.

Figure 6:
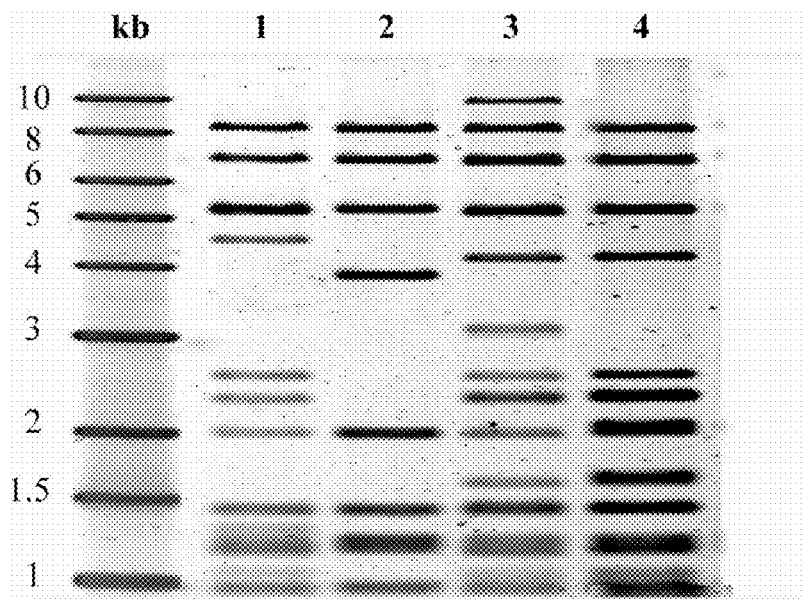

FIG. 6 illustrates NcoI digestion patterns of pSTM3 transformed into *E. coli*. Of the total DNAs examined, four types of band patterns emerged and are shown in lanes 1-4, respectively.

Figure 7:
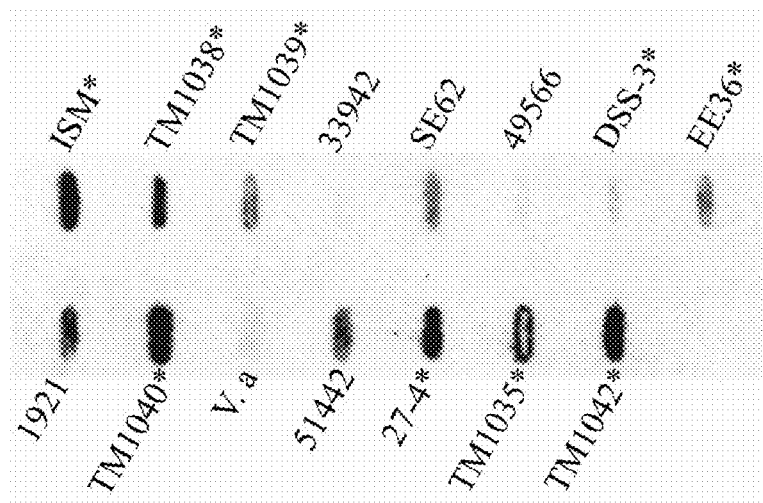

FIG. 7 demonstrates that DNA from other *roseobacter* species hybridizes to tda DNA. Total DNA was extracted from 13 *roseobacters*, TM1040, and a non-*roseobacter* control species (*V. anguillarum*), and used in a slot blot hybridization with labeled tda DNA. Positive hybridization was strongly correlated with measurable antibiotic activity (indicated by *). The strains used were: ISM: *Roseovarius* strain ISM; TM1038: *Roseobacter* sp. strain TM1038; TM1039, *Roseobacter* sp. strain TM1039; 33942, *Roseobacter denitrificans* ATCC 33942; SE62, *Sulfitobacter* strain SE62; 49566, *Roseobacter litoralis* ATCC 49566; DSS-3, *Silicibacter pomeroyi* DSS-3; EE36, *Sulfitobacter* strain EE36; 1921, *Sulfitobacter* strain 1921; TM1040, *Silicibacter* sp. TM1040; V. a, *Vibrio anguillarum;* 51442, *Roseobacter algicola* ATCC 51442; 27-4, *Phaeobacter* 27-4; TM1035, *Roseovarius* sp. strain TM1035; and, TM1042, *Roseovarius* sp. strain TM1042.

Figure 8:
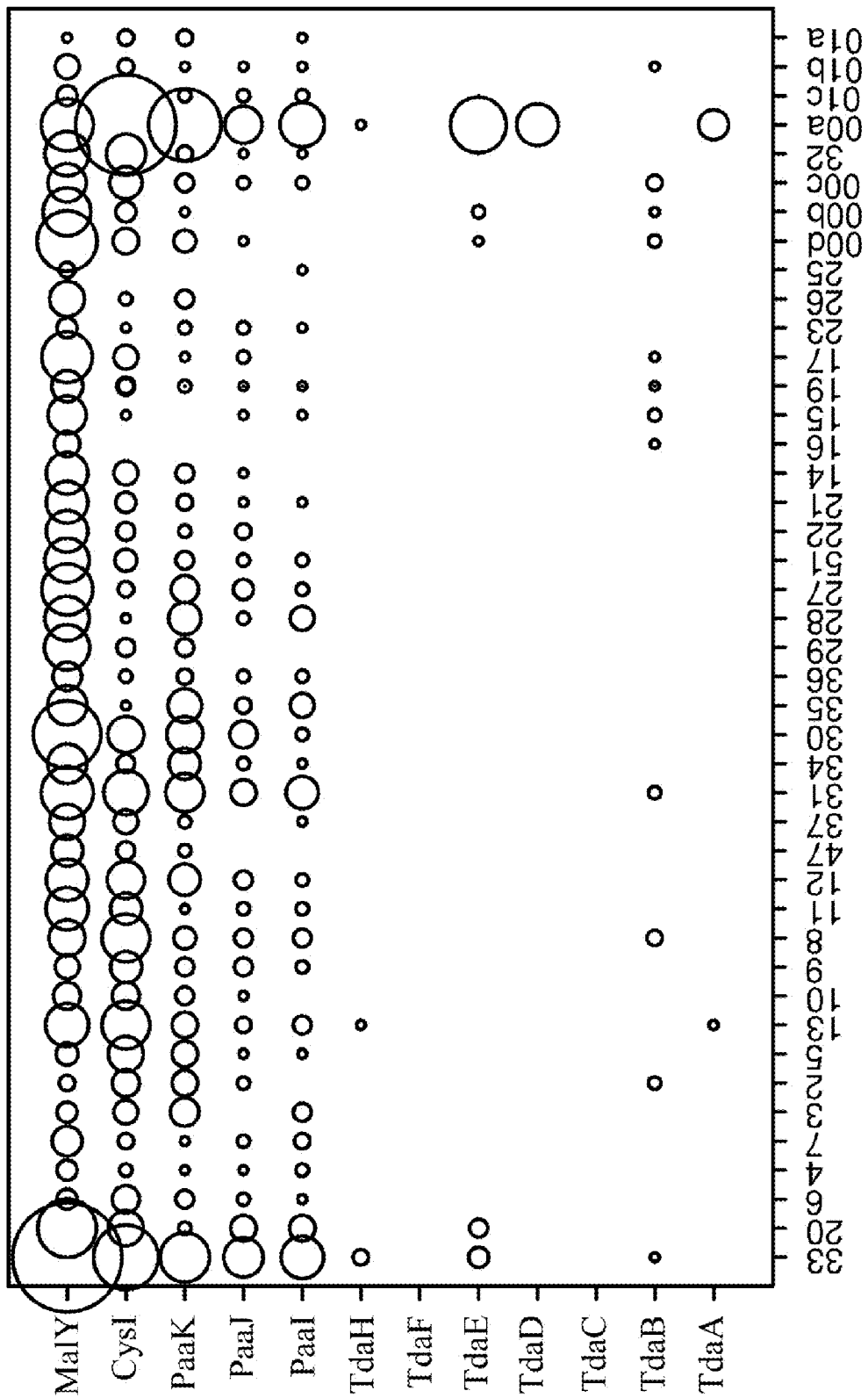

FIG. 8 illustrates the presence and relative abundance of each of the Tda proteins identified in TM1040 (rows) in the GOS metagenomic database (via the internet website at hypertext transfer protocol address, camera.calit2.net/). The relative abundance is based on the total BLASTP matching sequences in the individual filters using a cutoff E value of 1E-20 (Rusch, D. B., et al. *PLoS Biol.* (2007) 5:e77). The distribution of Tda proteins harbored on pSTM3 (TdaA-F) in the sample is remarkably different from the distribution of Paa and sulfur metabolism proteins (CysI, MalY, and TdaH), which have a more even distribution throughout the series of samples. Relative abundance is indicated by the size of the circle. GOS sample numbers are indicated on the horizontal axis.

Figure 9:
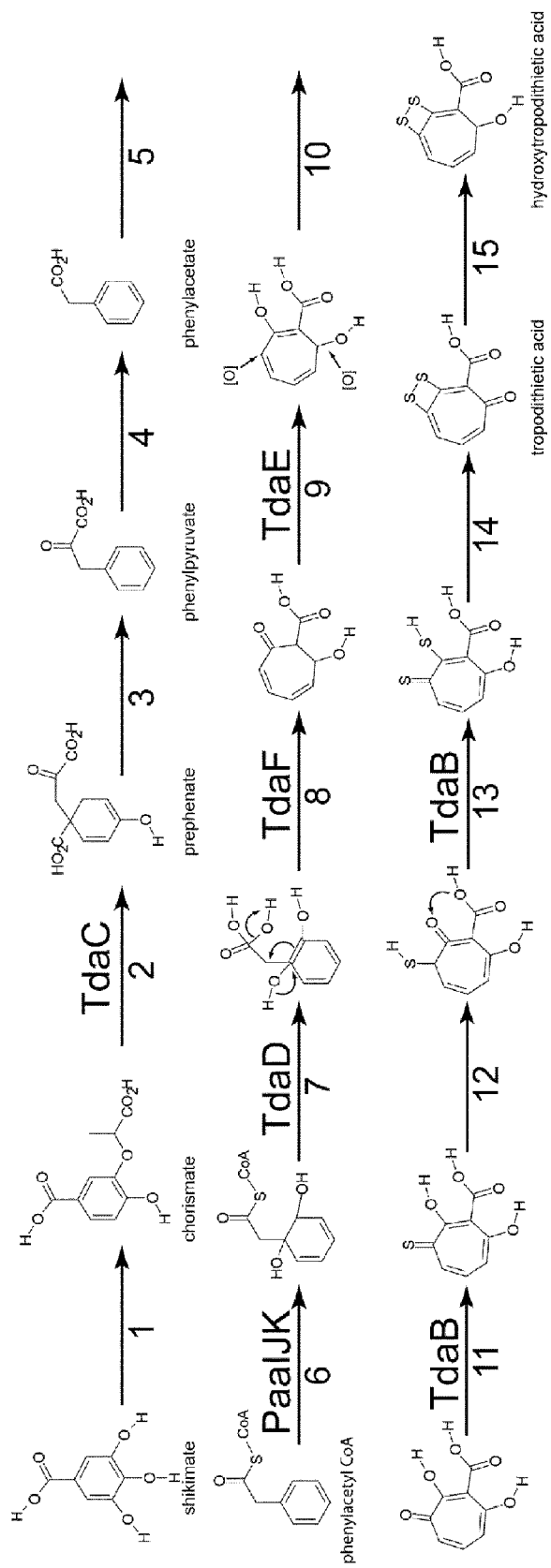

FIG. 9 provides a putative model of the TDA biosynthetic pathway.

Figure 10:
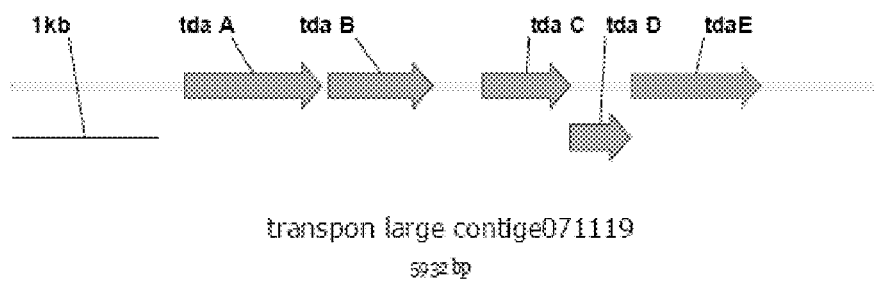

FIG. 10 is an illustration of SEQ ID NO: 7, showing the pSTM3 partial sequence contig tdaA~tdaE.

Figure 11:
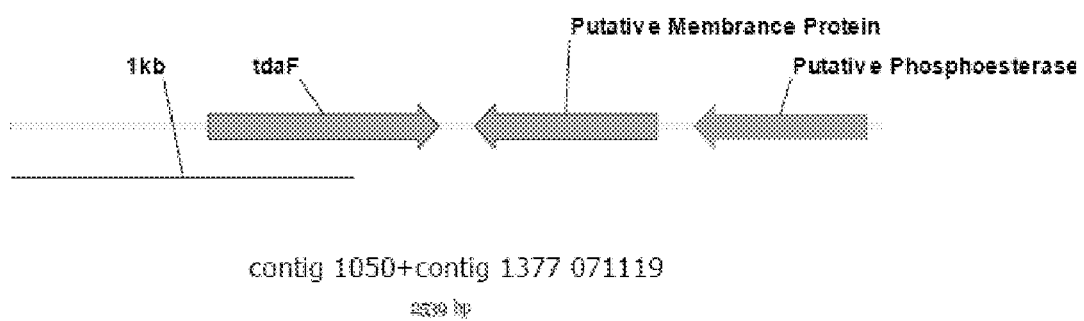

FIG. 11 is an illustration of SEQ ID NO: 8, showing the pSTM3 partial sequence tdaF and membrane protein gene.

Figure 12:
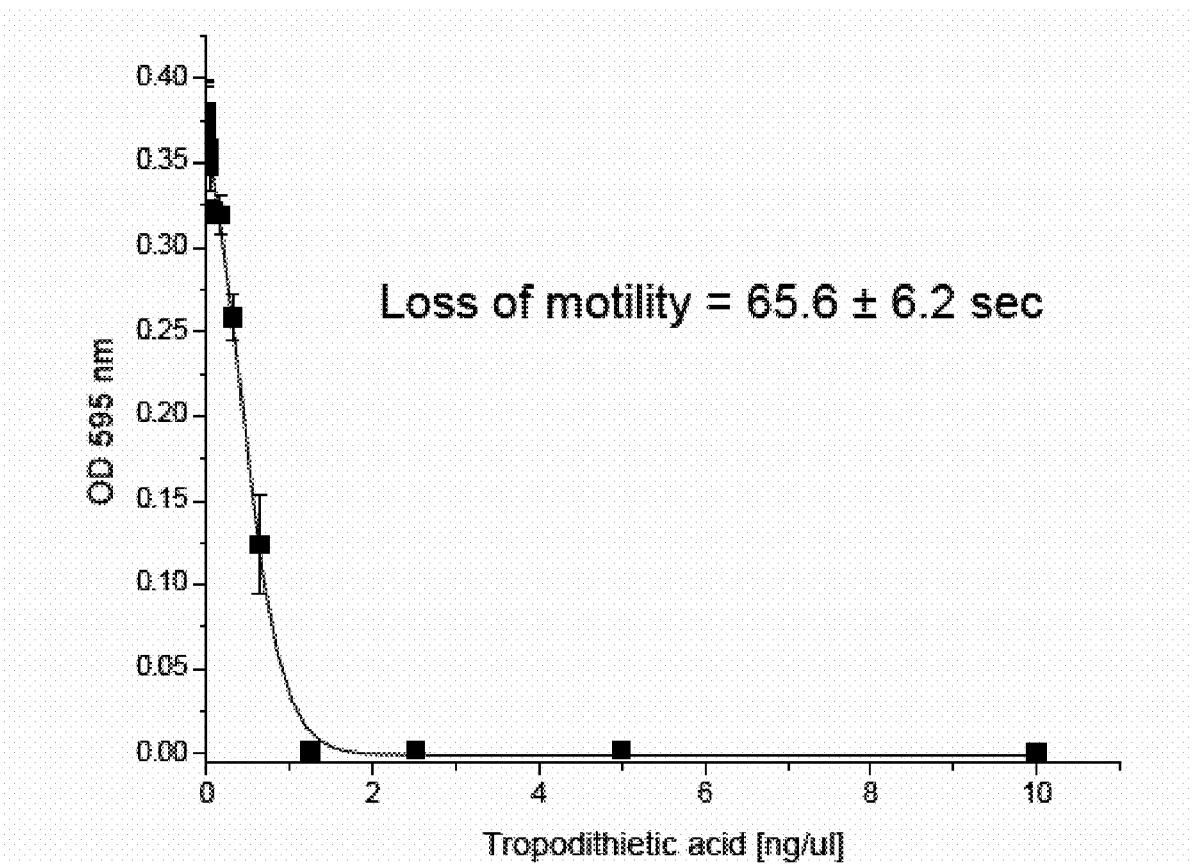

FIG. 12 is a graph showing the efficacy of TDA against *Vibrio anguillarum*, as described in Example 10.

Figure 13:
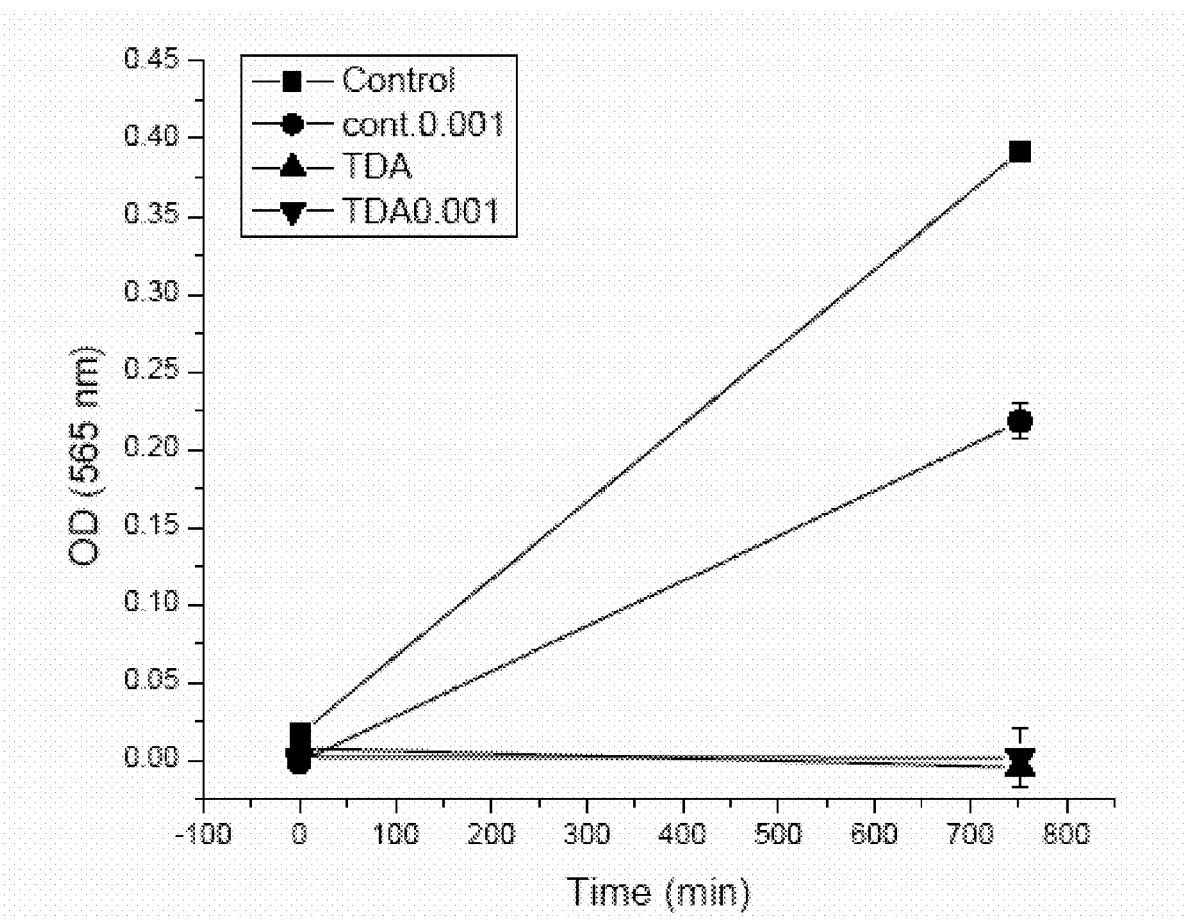

FIG. 13 is a graph showing the bactericidal character of TDA against *Vibrio anguillarum*, illustrating the results using control (squares; buffer only), control 0.001 (circles), TDA (triangles), and TDA 0.001 (inverted triangles), as described in Example 10.

DETAILED DESCRIPTION OF THE INVENTION

The present invention relates to *Roseobacter* bacteria and to the production of tropodithietic acid (TDA) by use of such microbial species.

The symbiotic association between the *roseobacter Silicibacter* sp. TM1040 and the dinoflagellate *Pfiesteria piscicida* involves bacterial chemotaxis to dinoflagellate-produced dimethylsulfoniopropionate (DMSP), DMSP demethylation, and ultimately a biofilm on the surface of the host. Biofilm formation is coincident with the production of an antibiotic and a yellow-brown pigment. The antibiotic is a sulfur-containing compound, tropodithietic acid (TDA). Using random transposon insertion mutagenesis, 12 genes were identified as critical for TDA biosynthesis by the bacteria, and mutation in any one of these results in loss of antibiotic activity (Tda$^-$) and pigment production. Unexpectedly, six of the genes, referred to as tdaA-F, could not be found on the annotated TM1040 genome and were instead located on a previously unidentified cryptic megaplasmid (ca. 130 kB; pSTM3) that exhibited a low frequency of spontaneous loss. Homologs of tdaA and tdaB from *Silicibacter* sp. TM1040 were identified by mutagenesis in another TDA-producing producing *roseobacter, Phaeobacter* 27-4, which also possesses two large plasmids (ca. 60 and ca. 70 kb, respectively), and tda genes were found by DNA:DNA hybridization in 88% of a diverse collection of 9 *roseobacters* with known antibiotic activity. These data suggest that *roseobacters* employ a common pathway for TDA biosynthesis that involves plasmid-encoded proteins. Using metagenomic library databases and a bioinformatics approach, a pronounced difference in the biogeographical distribution between the critical TDA synthesis genes was observed, implying substantial environmental preference differences among these genes.

The present invention in one specific aspect relates to the interaction of a *roseobacter, Silicibacter* sp. TM1040, and *Pfiesteria piscicida*. *Silicibacter* sp. TM1040 (hereafter referred to as TM1040) is isolatable from laboratory microcosm culture of heterotrophic DMSP-producing dinoflagellate *P. piscicida*. Marine algae are major producers of DMSP in the marine environment while members of the *Roseobacter* clade are capable of DMSP catabolism. TM1040 degrades DMSP via a demethylation pathway producing 3-methylmercaptopropionate (MMPA) as a major breakdown product. The bacteria respond via chemotaxis to dinoflagellate homogenates, and are specifically attracted to DMSP, methionine, and valine. TM1040 motility is important in the initial phases of the symbiosis. Once the bacteria are in close proximity to their host, TM1040 forms a biofilm on the surface of the dinoflagellate. The symbiosis includes two parts: one that involves chemotaxis and motility, and a second step in which a biofilm predominates.

Specific phenotypes, e.g., the ability to produce antibacterial compounds and biofilm formation, may give members of the *Roseobacter* clade a selective advantage, and help to explain the dominance of members of this clade in association with marine algae. The production of an antibiotic activity is observed in *roseobacters* and is hypothesized to provide an advantage when colonizing phytoplanktonic hosts, such as dinoflagellates. The genome of TM1040 consists of a 3.2 Mb chromosome and two plasmids, pSTM1 (823 Kb) and pSTM2 (131 Kb) (Moran, M. et al. *Appl. Environ. Microbiol.* (2007) 73:4559-4569). A comparison between TM1040 and two other *roseobacters* (*Silicibacter pomeroyi* DSS-3 and *Jannaschia* sp. CSS-1) suggests that *roseobacters* have abundant and diverse transporters, complex regulatory systems, multiple pathways for acquiring carbon and energy in seawater, and the potential to produce secondary, biologically active metabolites.

Biologically active metabolites, including antibacterial compounds, are obtainable from *roseobacters*. A sulfur-containing antibiotic compound, tropodithietic acid (TDA), has been isolated and chemically characterized from *Phaeobacter* 27-4, hereafter called 27-4, and *Roseobacter* T5. The chemical backbone of TDA (shown in FIG. 2) is a seven member aromatic tropolone ring, which is highly significant as tropolone derivatives, notably hydroxylated forms, are widely seen as medically important sources of antibacterial, antifungal, antiviral, and antiparasitic agents. Thiotropocin, another tropothione derivative closely related to TDA, can be synthesized from shikimate by an oxidative ring expansion of phenylacetic acid.

Both genomic and genetic techniques were used to identify the genes and proteins required for TDA synthesis in TM1040 and 27-4 as models for the *Roseobacter* clade. In the process of locating these genes, a megaplasmid critical for TDA biosynthesis that is part of the TM1040 genome was discovered by the present inventors, as hereinafter more fully described.

As set forth in more detail below, in one embodiment the invention provides an antibacterial composition comprising TDA, where the antibacterial composition is effective against *Vibrio anguillarium*, *Vibrio cholerae*, *Vibrio coralliilyticus*, *Vibrio shiloi*, *Halomonas* spp., *Mycobacterium marinum*, *Mycobacterium tuberculosis*, *Pseudomonas elongate*, *Spongiobacter nikelotolerans*, or *Staphylococcus aureus* (MRSA). By the work reported herein, the present inventors were able to show the bactericidal activity of TDA. Such antibacterial compositions, are useful in methods such as treatment of a bacterial infection, where administration of the antibacterial composition is effective in treating the bacterial infection, where the infection is caused by any of *Vibrio anguillarium*, *Vibrio cholerae*, *Vibrio coralliilyticus*, *Vibrio shiloi*, *Halomonas* spp., *Mycobacterium marinum*, *Mycobacterium tuberculosis*, *Pseudomonas elongate*, *Spongiobacter nikelotolerans*, and *Staphylococcus aureus* (MRSA).

TM1040 Produces the Sulfur-Containing Antibiotic Tropodithietic Acid

Figure 1:
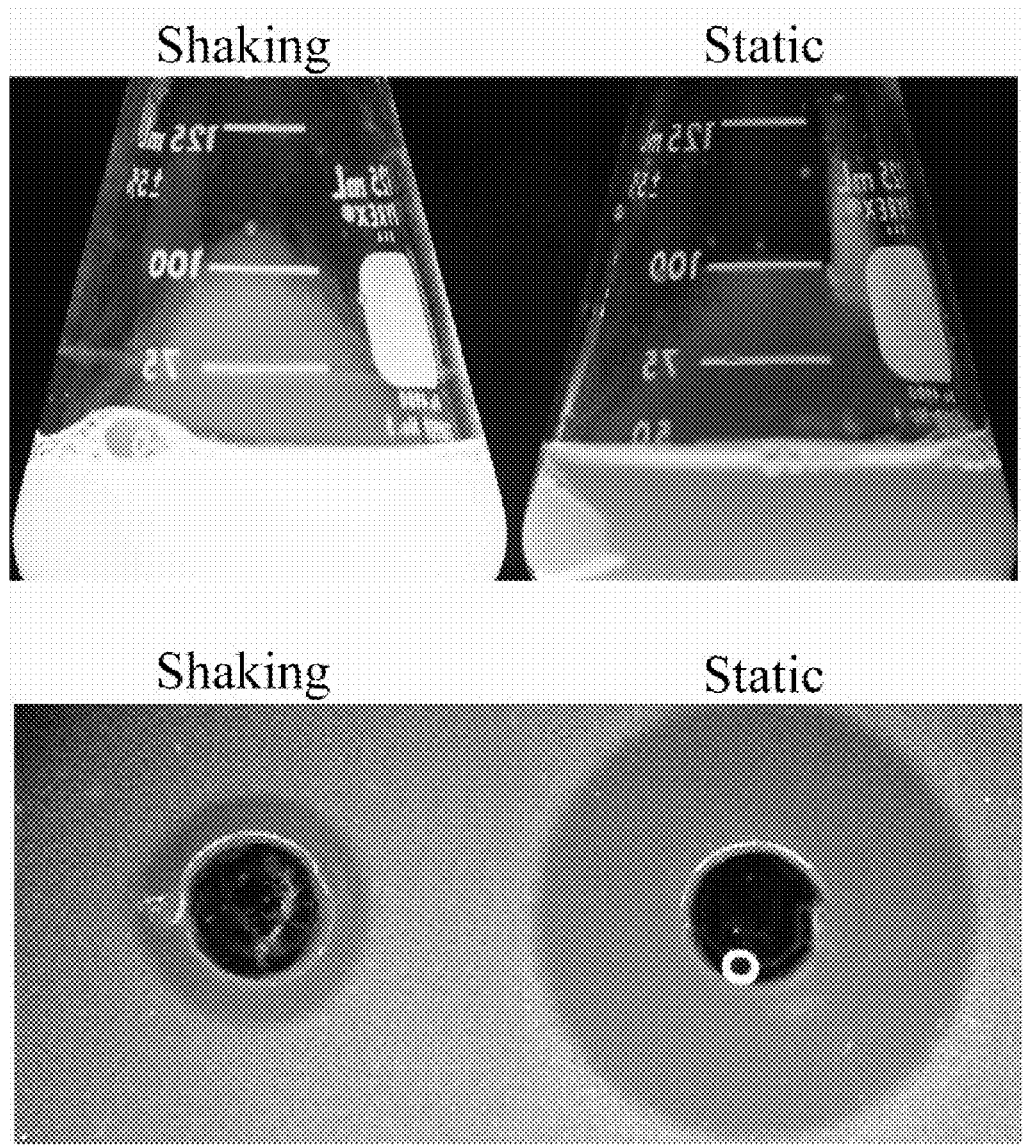
FIG. 1 provides a comparison of *Silicibacter* sp. strain TM1040 grown in a static environment versus with shaking and evaluated for antibacterial activity against *V. anguillarum*.

TM1040 produces an extracellular broad spectrum antibacterial compound capable of inhibiting or killing many bacteria. It was found that greater antibacterial activity occurred when the bacteria were grown in a nutrient broth culture under static conditions, i.e., no shaking, compared to shaking conditions (11 mm; FIG. 1). Under static conditions, TM1040 cells attached to one another forming rosettes and produced a very distinct yellow-brown pigment (FIG. 1). The *Silicibacter* sp. TM1040 grown in static liquid media has a large amount of antibacterial activity, which was measured by a well diffusion assay using *Vibrio anguillarium* as the target organism (FIG. 1). In contrast, pigment and antibacterial activity are both very low under 30° C. shaking conditions.

These phenotypes are consistent with *Phaeobacter* 27-4 and other *roseobacters*. During the course of this investigation, non-pigmented colonies were sometimes seen after TM1040 was incubated on nutrient agar, and subsequent analysis revealed that these 'white spontaneous mutants' also had lost antibacterial activity as well.

TM1040 produces an antibiotic and shares common phenotypic traits with other *roseobacters*, notably *Phaeobacter* 27-4 whose antibiotic is tropodithietic acid (TDA). It was therefore hypothesized that the antibacterial compound produced by TM1040 may also be tropodithietic acid.

Figure 2:
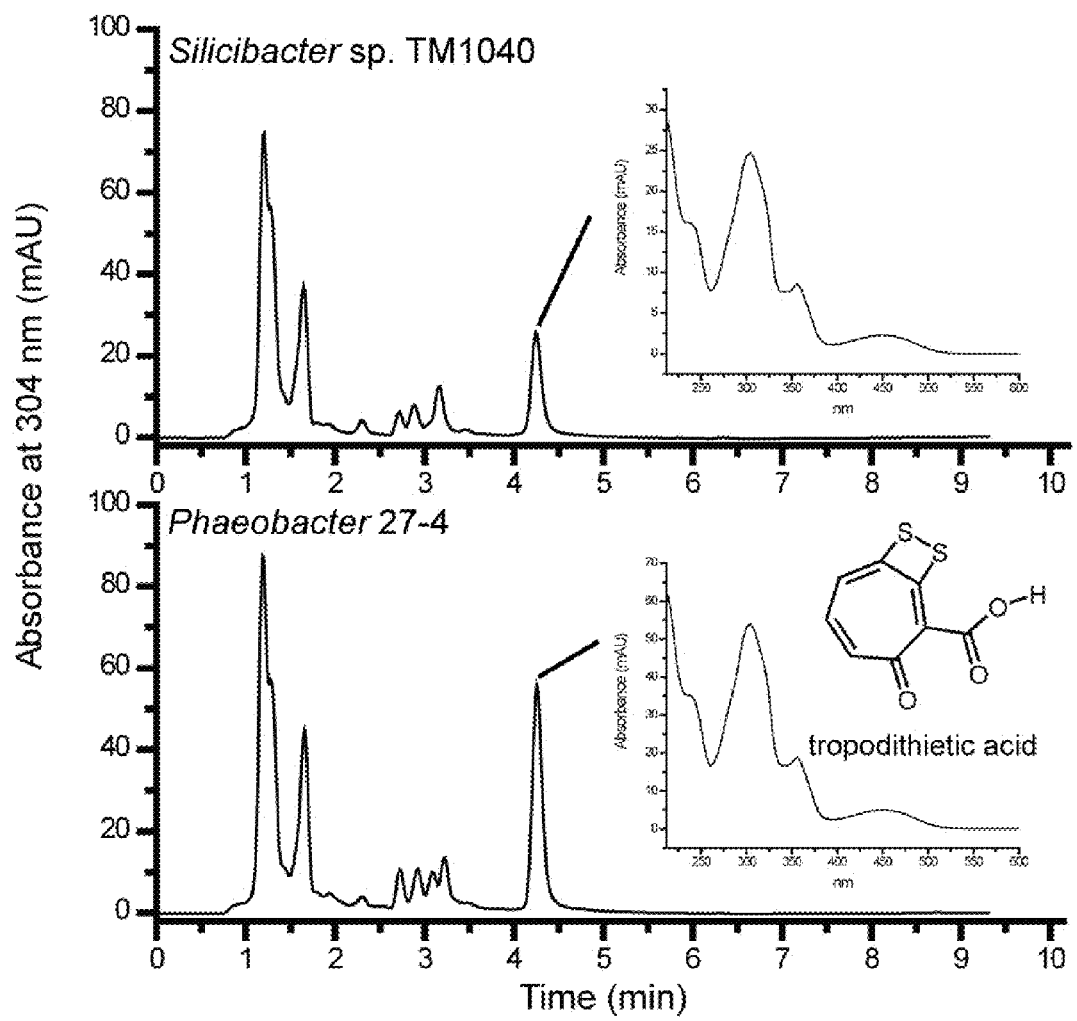
FIG. 2 provides C18 reverse phase HPLC chromatograms of ethyl acetate extracts from TM1040 and *Phaeobacter* 27-4.

Example 2 describes characterization of the antibiotic produced by the bacteria of Example 1. Cell-free supernatants were collected independently from both TM1040 and 27-4, ethyl acetate extraction of the supernatants was used to separate TDA from other compounds, and the concentrated extract was analyzed by HPLC. The resulting elution chromatograms and subsequent UV spectra of the putative peak of TDA from TM1040 and 27-4 are shown in FIG. 2. Both chromatograms and UV spectra are nearly identical, indicating chemically similar metabolites are produced by both strains. A compound with a retention time of 4.2 min (indicated in FIG. 2) is observed in both chromatograms and has been positively identified as TDA in 27-4. The equivalent 'TDA peak' from TM1040 has a UV spectrum that overlaps with that of published spectrum of TDA obtained from 27-4, with four major absorptions at 210 nm, 304 nm, 355 nm and 452 nm. Mass spectroscopy of the TM1040 'TDA peak' was used to confirm the efficacy of the compound as TDA. Taken together, the data corroborate TDA as the antibacterial metabolite produced by TM1040.

Identification of Genes Involved in the Synthesis of TDA

With the exception of genes involved in shikimate and phenylacetate metabolism, an analysis of the genome of TM1040 does not provide much insight into genes likely to participate in the biosynthesis and regulation of TDA. To determine the genes required for TDA synthesis, a genome-wide random-insertion transposon bank of 11,284 Kan$^r$ colonies was generated in TM1040 and screened for antibiotic loss-of-function mutants (Tda$^-$ phenotype), as described in Example 3. Approximately 0.7% of the transposon insertions (81 out of 11,284) were Tda$^-$ mutants, all of which were defective in TDA synthesis as well as in pigment formation.

The location of the transposon insertion site in each of the 81 Tda$^-$ mutants was determined by sequencing TM1040 DNA adjacent to the transposon. The pair of sequences (both sides of the transposon insertion point) obtained from each mutant was used to search the annotated TM1040 genome to identify the mutated gene. Surprisingly, homologs were not found in the genome for 32 or nearly 40% of the Tda$^-$ mutants, yet these DNAs overlapped permitting assembly into one large contiguous DNA fragment of 4.5 kb harboring at least 6 ORFs, called tdaA-F (Table 2 and FIG. 3A). FIG. 3A shows sulfur assimilation genes, tdaH, malY, cysI, located in the TM1040 chromosome. Phenylacetate catabolism genes are in the megaplasmid pSTM1. It is clear that tdaA-F represent DNA that is not part of the original annotation of the genome, suggesting that this DNA may have been lost from the sequenced variant of TM1040. A thorough analysis of these 'orphan' genes is presented below (TDA biosynthesis genes resided on a 130 kb cryptic plasmid).

Forty nine Tda$^-$ mutants had transposon insertions in genes found in one of the three DNAs that make up the genome. Due to the observation of a low frequency spontaneous loss of TDA synthesis and knowledge of the existence of tdaA-F, each of the 49 genomic Tda$^-$ strains was analyzed for the presence of tdaA-F. Nearly 90% (43 out of 49) did not harbor tdaA-F, as determined by PCR amplification with primers to tdaE, and had lost this DNA presumably resulting in their Tda$^-$ phenotype. The transposon insertion in these strains may contribute to the Tda$^-$ phenotype.

The sequences obtained from the remaining 6 Tda$^-$ mutants were highly informative (Table 2).

An analysis of the genes identified from the 6 'genomic' TDA$^-$ mutants revealed that the phenylacetate catabolism (paa) pathway is required for TDA synthesis (FIG. 3A). Transposon insertions were identified in homologs of paaI, paaJ, and paaK. The deduced amino acid sequence from each of these ORFs had strong homology to similar proteins encoded by other *roseobacters*. For example, TM1040 paaI is 79% similar to paaI of *Silicibacter pomeroyi* DSS-3, TM1040 paaJ is 74% similar to an ORF of *Roseobacter* sp. MED193, and paaK is 77% to *Roseobacter* sp. MED193 paaK (Table 2). In other bacteria, paaGHIJK encodes a ring-hydroxylating complex of proteins that is responsible for the first step in the aerobic catabolism of phenylacetate involving Coenzyme A (CoA) activation, producing 1,2-dihydro-phenylacetate-CoA. The finding that mutations in paa genes affects TDA synthesis is consistent with the biochemical evidence of phenylacetate metabolism in thiotropocin synthesis.

Mutants with defects in phenylacetate metabolism were also unable to grow on phenylalanine, phenylacetic acid, tryptophan, sodium phenylpyruvate or phenylbutyrate as a sole carbon source (Table 3).

TDA is a disulfide-modified tropolone compound, indicating that sulfur metabolism must be involved in TDA synthesis. This hypothesis is supported by the identification of 3 Tda⁻ mutants (Table 2) each with a transposon inserted in a gene whose product is involved in sulfur metabolism: cysI, malY, and an ORF (tdaH) with homology to sulfite oxidase (Table 2). The identification of these genes suggests that sulfur from reductive sulfur pathways is used and incorporated into TDA, which was tested by observing growth of the sulfur-metabolism mutants on a minimal medium containing a sole sulfur source (Example 4).

TM1040 (inverted triangles) and the cysI mutant (HG1220; circles) were grown in minimal medium containing either methionine (closed symbols) or methionine (open symbols), and growth was measured optically at 600 nm. Unlike the wild-type, the CysI⁻ mutant cannot grow methionine, but does utilize cysteine. Measurement of antibiotic activity indicates that the cysI defect also affects TDA synthesis, which is corrected by the addition of cysteine to the medium, but not methionine, DMSP, sulfite, or sulfate addition (Table 2). The results are shown in FIG. 4. The cysI mutant grew when provided complex sulfur sources or cysteine and was unable to utilize DMSP, $SO_3^{2-}$, $SO_4^{2-}$, or methionine. The addition of cysteine to the medium resulted in enhanced growth of the cysI mutant as well as increased synthesis of TDA (FIG. 4).

TDA Biosynthesis Gene Resided on a 130-kb Cryptic Plasmid

As previously described, tdaA-F genes were not part of the annotated TM1040 genome and were absent in spontaneous Tda⁻ mutants. A series of bioinformatic analyses was conducted to elucidate the potential function of these genes (Table 2) and their proteins. Interestingly, these genes share their strongest homology with a similar set of genes in *Paracoccus denitrificans* PD1222 chromosome 1 (Accession number: NC_008686), a non-motile alphaproteobacterium first isolated from soil by Beijerinck. As shown in FIG. 3B, the orientation and spacing between tdaA and tdaB suggests that these genes form a bicistronic message while tdaC-E are likely to compose an operon separate from tdaAB. tdaF is in a different operon (FIG. 3). In FIG. 3B, tdaH encodes sulfite oxidase domain protein; hik2 encodes two-component hybrid sensor and regulator; malY encodes β-C-S lyase (cystathionase); asnC encodes transcriptional regulator AsnC family; cysG encodes siroheme synthesis; hypo encodes hypothetical protein; cysI encodes sulfite reductase beta (siroheme-dependent); cysH encodes adenylylsulfate reductase; gntR encodes GntR family transcriptional regulator; paaG, paaH, paaI, paaJ, paaK encode respectively phenylacetic acid degradation protein complex protein 1,2,3,4,5; tdaA encodes LysR substrate binding domain protein; tdaB encodes β-etherase; glutathione-S-transferase; tdaC encodes prephenate dehydratase; tdaD, 4-hydroxybenzoyl-CoA thioesterase; tdaE encodes Acyl-CoA dehydrogenase; tdaF encodes phosphopantothenoylcysteine decarboxylase. *P. denitrificans* PD1222 genome contains two chromosomes and one plasmid, whereas tdaAB, tdaCDE and tdaF homologue genes located discretely in a 19 kb region of chromosome 1.

Amino acid domain identification was useful in assigning potential functions to the encoded proteins. For example, TdaA (Table 2) has homology with LysR regulatory proteins, possessing a helix-turn-helix and a LysR substrate-binding domain (Zaim, J., et al. *Nucleic Acids Res*. (2003) 31:1444-1454). TdaA is the only regulatory protein uncovered in this study, perhaps indicating that it is the sole regulator of TDA synthesis. The remaining ORFs encode putative enzymes. TdaB contains a glutathione S-transferase (GST) domain and belongs to the bacterial GST protein family (Table 1). TdaC has an amino acid domain with homology to prephenate dehydratase (PheA), an enzyme involved in the conversion of chorismate to prephenate, a step in the pathway leading to phenylacetate synthesis.

The involvement of CoA metabolism, addition, or modification is evident from the functional domains on TdaD and TdaE. TdaD is anticipated to be a member of the thioesterase superfamily of acyl-CoA thioesterases (Table 2), TdaE encodes a putative acyl-CoA dehydrogenase (ACAD), and TdaF has homology to aldehyde dehydrogenase.

The secondary evidence suggests that tdaA-F resides on a cryptic plasmid that may be spontaneously lost. To develop a means to test the hypothesis, three strains, TM1040, a spontaneous Tda⁻ nonpigmented strain of TM1040 (TM1040SM), and HG1265 (tdaE::Tn) (Table 1) were used. FIG. 5A illustrates pigment analysis of the three strains, where TM1040 (wt) produces a yellow-brown extracellular pigment that is correlated with TDA synthesis. In contrast, a tdaE:Tn mutant (strain HG1265) and a spontaneous mutant (sm; TM1040SM) are nonpigmented and have lost the ability to produce both TDA and pigment. Spontaneous loss of pigment and antibiotic activity results from a loss of tda genes.

PCR amplification using primers for tdaA-E, was performed, and predicted to generate a 3.8 kb product from wild-type DNA. As shown in FIG. 5B, PCR amplification of wild-type DNA gave the predicted 3.8 kb band, a 5.7 kb product when tdaE:Tn DNA was used as a template, with the additional 2 kb in size of the tdaE:Tn product resulting from insertion of the transposon, and no product when the DNA from the SM strain was amplified indicating that the SM strain had lost the tdaA-E locus.

Total DNA from TM1040, TM1040SM, and HG1265 (tda-E:Tn) was separated by PFGE. As observed in FIG. 5C, all three strains had high molecular weight DNA, presumably a mixture of chromosomal and pSTM1 and a band or bands at ca. 130 kb, corresponding to the size of pSTM2 (132 kb) (Moran, M. A., et al. *Appl. Environ. Microbiol.* (2007) 73:4559-4569). Close inspection of this region and comparison between the SM DNA lane (middle, FIG. 5C) and either the TM1040 or tdaE:Tn DNA (left and right lanes, respectively) shows that the SM band is thinner than either TM1040 or tdaE:Tn hinting that SM DNA is missing a DNA species in this size range that overlaps with pSTM2. Repeated attempts to change PFGE conditions did not resolve this region. To overcome this limitation, a Southern blot (FIG. 5D) using a tdaD DNA probe was performed on the gel shown in FIG. 5C, and the results confirmed that the SM DNA, while possessing a 130 kb band, fails to hybridize to tdaD. In contrast, both wild-type DNA and tdaE:Tn DNA hybridize to the expected band (ca. 130 kb). This confirms the loss of tda DNA in SM and adds evidence supporting the hypothesis that the missing tda DNA is on a plasmid. It does not rule out the unlikely possibility that tda genes reside on pSTM2 and are somehow deleted from that known molecule.

To resolve the issue, plasmids were isolated from each of the three strains (TM1040, TM1040SM, and HG1265) and subjected each mixture to NcoI digestion (FIG. 5E), chosen because an in silico NcoI digestion of pSTM2 provided a recognizable pattern of DNA fragments. The digested DNAs were separated by electrophoresis and the band patterns compared to each other and to an in silico NcoI digestion of pSTM2 (supplemental data). The pattern of fragments from sm DNA matched the predicted pSTM2 NcoI digestion, while both wt and tdaE DNA patterns showed evidence of additional restriction fragments. As shown in FIG. 5E, the TM1040SM DNA digest had much fewer bands than wild-type DNA or DNA from tdaE:Tn. This would be expected if the TM1040SM strain lost a large plasmid. Consistent with this hypothesis, Southern blotting showed that a tdaD probe hybridized to a 4.5 kb fragment in wild-type plasmid DNA and to a 6.4 kb fragment from plasmids isolated from the tdaE:Tn strain. A tdaE probe hybridizes to one fragment in wt and tdaE:Tn DNA cut with NcoI, but to any fragments produced from NcoI digestion of plasmid. The increase in the size of the fragment in tdaE:Tn results from the insertion of the 2 kb transposon. (FIG. 5F).

It was reasoned that it is possible to transform a cryptic tda plasmid bearing a selectable marker into a suitable host and thereby provide proof of the existence of this plasmid. The transposon used, EZ:Tn, contains a kanamycin-resistance gene as well as the oriR6K origin of replication permitting replication in permissive hosts carrying the pir gene. Thus, the plasmid from tdaE:Tn was used to transform *E. coli* EC100D (Table 1) with a subsequent selection for kanamycin resistance. This transformation was successful despite a very low transformation efficiency resulting in 7 Colony Forming Units (CFUs) per μg of mixed plasmid DNA, and provides strong evidence for the existence of a cryptic ca. 130 kb plasmid harboring tda genes. This new plasmid was called pSTM3.

Twelve random colonies were chosen from the transformation with pSTM3 and the NcoI-digestion pattern of each compared. FIG. 6 shows the four common patterns resulting from this analysis. Although each plasmid was PCR positive for the tda genes (data not shown) and the set of four shared many common bands, they had remarkably different patterns indicating deletion and/or rearrangements had occurred during or after transfer of pSTM3 to *E. coli*.

A mixture of plasmid pSTM3-1265 (pSTM3 harboring a transposon in tdaE) and pSTM2 was isolated from HG1265 and the DNAs used to transform *E. coli*. Each of the plasmids harbored in the resulting Kan$^r$ transformants was purified, digested with NcoI, and the resulting DNA fragments separated by agarose gel electrophoresis.

The sum of the results indicates that TM1040 harbors a ca. 130 kb plasmid, pSTM3, which is essential for TDA and pigment biosynthesis and which may be spontaneously lost in laboratory culture.

Distribution of tda genes in other *Roseobacters*

The *Roseobacter* clade produce an antibacterial activity. In light of the current findings, confirmation was sought that other *roseobacters* had tda genes as well, and *Phaeobacter* 27-4 was chosen as a suitable candidate. (Example 8)

The same transposon was used to construct a 6,321-member library and was screened for the Tda$^-$ phenotype. 37 Tda$^-$ mutants were found of which 12 were analyzed further. Two of the 12 ORFs mutated were similar to TdaA (identity 38%) and TdaB (identity 55%) from TM1040 (Table 4), suggesting that these two *roseobacters* share a common TDA biosynthesis and regulation scheme. The remaining 9 genes were not identified as important to TDA synthesis in TM1040 and had varying degrees of homology to genes in the annotated TM1040 genome, but, unlike TM1040, were not part of the phenylacetate or reductive sulfur pathways. The one exception is 27-4 metF (Table 4), which may possibly be involved in sulfur metabolism.

DNA:DNA hybridization was also used to measure hybridization of a tdaA-F gene probe to DNA from 14 *Roseobacter* clade species (FIG. 7). The tda probe hybridized to 8 of the 9 *roseobacters* that have been established as producing antibacterial activity (FIG. 7), with the ninth, *Silicibacter pomeroyi* DSS-3, showing a low amount of hybridization. Three of 6 non-antibiotic-producing *roseobacters* also positively hybridized to the tda DNA. This false positive may have resulted from a strain that has very low tda expression and antibiotic activity below the detection limits of the well diffusion assay, or from spurious hybridization to non-tda DNA. The tda probe did not hybridize with DNA from *V. anguillarum*, implying that the second possibility is the more likely scenario.

TABLE 4

*Phaeobacter* 27-4 genes and encoded proteins required for the regulation and synthesis of tropodithietic acid.

| Mutant Number | GenBank Accession Number | Gene Designation | Function | Best Hit Ortholog/E score |
|---|---|---|---|---|
| Ring Precursors, Oxidation, and Expansion | | | | |
| JBB1001/ JBB1030 | EF139212 | tdaB | β-etherase, glutathione S transferase | *Sinorhizobium meliloti* putative β-etherase (β-aryl ether cleaving enzyme/4e−52 |
| Sulfur Metabolism and Addition | | | | |
| JBB1044 | EF139218 | metF | 5-methyltetrahydrofolate--homocysteine S-methyltransferase | *Silicibacter* sp. TM1040 MetF protein/2e−77 |
| Co-enzyme A Metabolism | | | | |
| JBB1009 | EF139215 | tdbA | D-β-hydroxybutyrate dehydrogenase | *Roseovarius* sp. 217 D-β-hydroxybutyrate dehydrogenase/2e−32 |
| JBB1045 | EF139216 | tdbB | Phosphate acetyltransferase | *Roseobacter* sp. MED193 phosphate acetyltransferase/8e−81 |

TABLE 4-continued

*Phaeobacter* 27-4 genes and encoded proteins required for the regulation and synthesis of tropodithietic acid.

| Mutant Number | GenBank Accession Number | Gene Designation | Function | Best Hit Ortholog/E score |
|---|---|---|---|---|
| | | | Transport: Import and Export | |
| JBB1003 | EF139213 | tdbC | Lytic transglycosylase, peptidase C14 | *Roseobacter* sp. MED193 hypothetical protein/6e−85 |
| JBB1005 | EF139221 | traI | TraI, Type IV (Vir-like) secretion | *Rhodobacter sphaeroides* 2.4.1 TraI/5e−58 |
| JBB1011 | EF139222 | tdbD | Type I secretion target repeat protein | *Roseobacter* sp. MED193 type I secretion target repeat protein/8e−54 |
| JBB1029 | EF139216 | tdbE | Oligopeptide/dipeptide ABC transporter | *Silicibacter* sp. TM1040 binding-protein-dependent transport systems inner membrane component/6e−124 |
| | | | Regulatory Mechanism | |
| JBB1006 | EF139220 | clpX | ATP-dependent Clp protease | *Silicibacter* sp. TM1040 ATP-binding subunit ClpX/1e−47 |
| JBB1007 | EF139214 | tdbF | Ribonuclease D | *Roseobacter* sp. MED193 ribonuclease D/6e−49 |
| JBB1030 | EF139217 | tdaA | LysR substrate binding domain protein | *Paracoccus denitrificans* PD1222 regulatory protein, LysR:LysR, substrate-binding/3e−51 |

Distribution of tda Genes in the Environment

Marine genome and metagenomic databases were searched for sequences with homology to one of the 12 genes (Table 2) required for TDA synthesis by TM1040. While homologs to the proteins involved in phenylacetate and reductive sulfur metabolism were found within the 14 selected *roseobacter* genomes in Roseobase (hyper text transfer protocol world wide web address roseobase.org/) and the Gordon and Betty Moore Foundation Marine Microbial Genome databases (hyper text transfer protocol address research.venterinstitute.org/moore/), close homologs of TdaA-F were absent (at a BLASTP E value cutoff of 1E-30). While the reason for the absence of homologs is not known, it is possible, although unlikely, that all 14 *roseobacters* do not produce TDA, produce an antibacterial activity that involves another compound, or lost their tda plasmid. The last possibility is most likely to have resulted from laboratory culturing, therefore Tda homologs were searched for in environmental metagenomic libraries (hyper text transfer protocol camera.calit2.net/) that should contain abundant uncultivated *roseobacter* DNA.

The data gathered from searching the CAMERA marine metagenomic GOS dataset database are shown graphically in FIG. 8, where a circle and its relative size indicates the presence and abundance (respectively) of a given protein. As was observed with the *roseobacter* genomes, phenylacetate and reductive sulfur metabolism proteins were found at numerous sites, with the greatest abundance of PaaIJK and CysI at site GS00a, a Sargasso Sea sample (31 32'6" N, 63 35'42" W). Positive Tda protein 'hits' were also recorded in a hypersaline pond sample (GS033) and a sample obtained from Lake Gatun, Panama Canal (FIG. 8). In no sample were hits to all 12 proteins involved in TDA biosynthesis found.

Various members of the *Roseobacter* clade, whose genomes reveal a great potential for the synthesis of bioactive molecules, produce TDA. Many marine bacteria produce an antibiotic activity, including antibacterial activity from *roseobacters*, e.g., a compound that produces a probiotic effect on scallop larvae and is antagonistic to γ-Proteobacteria strains, as well as a compound that is antagonistic against fish larval bacterial pathogens. From the data, it is likely that much of the antibiotic activity seen in *roseobacters* is due to plasmid-borne tda genes that can be difficult to maintain in laboratory conditions.

There is a direct link between the spontaneous appearance of non-pigmented Tda⁻ colonies and the loss of pSTM3 of TM1040. Over 40 of the mutants initially screened as Tda⁻ were ultimately found to have lost pSTM3. This suggests that loss of pSTM3 is a relatively frequent event during laboratory cultivation of TM1040. Instability of the Tda⁺ phenotype is not unique to TM1040. The appearance of spontaneous non-pigmented Tda⁻ mutants or variants is characteristic of other *roseobacters*, including *Phaeobacter* 27-4 and *Roseobacter gallaeciensis* sp. T5. One possible explanation for the cause of these spontaneous mutants is a loss of a plasmid carrying one or more critical genes required for TDA synthesis. Indeed, 27-4 possesses at least two plasmids of ca. 60 kb and 70 kb respectively. One or both of these plasmids may be involved in TDA biosynthesis of 27-4 and tdaA and tdaB, identified by transposon insertion mutagenesis in 27-4 Tda⁻ mutants, reside on one of these plasmids.

Instability of pSTM3 is also apparent when the plasmid is transformed into a non*roseobacter* host, e.g., *E. coli*. As shown in FIG. 6, at least four unique NcoI-restriction fragment patterns were observed from pSTM3 that had been successfully transformed into a new host. As a cause of this instability, it seems improbable that TDA biosynthesis is to blame, because the pSTM3 used to transform *E. coli* does not confer a TDA⁺ phenotype due to the presence of a transposon in tdaE. It is possible that, despite absence of TdaE, some other protein(s) encoded by other tda genes (tdaABCD or -F) may be detrimental when expressed in *E. coli*. While there is no evidence to directly link instability of pSTM3 in *E. coli* with spontaneous loss of the plasmid in TM1040, these phenomena may share a common cause. Efforts have been initiated to sequence and annotate pSTM3 and compare it to the pSTM3 species obtained from *E. coli*. Preliminary evidence indicates that pSTM3 harbors a repC homolog upstream of tdaA. RepC forms a complex along with RepAB and is required for plasmid replication and maintenance. It will be determined if the pSTM3 plasmid species obtained from *E. coli* transformation have defects in repABC.

The ability of pSTM3 to replicate in *E. coli*, albeit with significant alteration in the plasmid, suggests that pSTM3 also may transferred to other marine bacteria, perhaps other *roseobacters*, or even to higher organisms, e.g., dinoflagellates. TM1040 possesses varied capabilities to achieve horizontal gene transfer, including the presence of several prophage genomes in the bacterium's genome, one of which is homologous to the gene transfer agent of other alphaproteobacteria, and many of genes on pSTM2 are homologs of the vir system of *Agrobacterium tumefaciens*. The *A. tumefaciens* Ti plasmid, transferred by Vir Type IV secretion, requires RepABC, suggesting that a similar mechanism may allow pSTM3 transfer to other organisms. Plasmids similar to pSTM3, such as pSymA of *Sinorhizobium meliloti* and the Ti plasmid, are important for the proper interaction of those bacteria and their respective hosts, and TM1040 pSTM3 and pSTM2 may correspondingly serve to enhance the TM1040-dinoflagellate symbiosis.

It is important to note that TDA activity and biosynthesis depend on culture conditions and the physiology of TM1040. TDA activity is significantly enhanced when TM1040 is cultured in a static nutrient broth, a condition that accentuates biofilm formation. The symbiosis includes two phases: the motile phase in which TM1040 cells actively respond to dinoflagellate-derived molecules by swimming towards the host, and sessile phase, whereupon having located the zoospore, the bacteria cease to be motile and form a biofilm on the surface of the dinoflagellate. Thus, there is a direct correlation between biofilm formation and TDA biosynthesis.

Biosynthesis of TDA has several potentially beneficial effects on the TM1040-dinoflagellate symbiosis. TDA is likely to benefit the dinoflagellate by acting as a probiotic with antibacterial activity whose action prevents the growth and colonization of bacteria on the surface of the dinoflagellate that could potentially harm the zoospore. In turn, the antibacterial activity of TDA may enhance the growth of TM1040 cells attached to the zoospore by warding off other biofilm-forming bacteria that compete with TM1040 for space on the surface of and nutrients from *P. piscicida*. Interestingly, DMSP appears not to be a primary source of the sulfur atoms of TDA. One or more non-DMSP sulfur-containing metabolites produced by the dinoflagellate may be used by TM1040 in the biosynthesis of TDA.

One of the unexpected results from this study is the paucity of homologous Tda proteins in either the genomes of other sequenced *roseobacters* or in the CAMERA metagenomic library (FIG. 8). There are several reasons why Tda proteins were not found. For example, amino acid sequence divergence between Tda proteins of TM1040 and other *roseobacters* could result in BLASTP E values greater than the chosen cutoff of 1E-20. This argument may also be applied to the metagenomics search. In focusing on just the search for Tda homologs in *roseobacter* genomes, it is possible that, in culturing these *roseobacter* species in preparation for isolation and purification of their genomic DNAs, the bacteria lost a pSTM3-like plasmid harboring tda genes. Equally feasible is the possibility that TDA is but one of many antibiotic compounds produced by *roseobacters* or that more than one biochemical pathway exists to produce TDA. Both arguments may help explain the lack of Tda protein homologs in *roseobacter* genomes.

The lack of Tda protein homologs in the marine metagenomics database presents a much more difficult problem to interpret, especially in the context of PaaIJK and CysI searches that frequently identified their respective homologs in numerous samples within the database (FIG. 8). While the data do not provide definitive answers to this question, the data show that stability and retention of pSTM3 by TM1040 is greatest when the bacteria are directly associated with the dinoflagellate, i.e., the plasmid may be lost when TM1040 is grown in laboratory culture, yet retained when cultivated as part of the *Pfiesteria piscicida* mesocosm from which the bacteria were isolated. Close association of TM1040 with *P. piscicida* provides a selection to maintain the pSTM3; that selective pressure is lost when the bacteria are taken away from their host (as happens under laboratory culture). The CAMERA metagenomic samples analyzed were prepared after filtration to remove 0.8 μm particles, which may have removed the portion of the *roseobacter* population harboring a tda plasmid like pSTM3.

The two metagenomic samples that showed relatively good Tda homolog hits were from a site in the Sargasso Sea and a hypersaline pond, respectively. DMSP is potentially useful by algae as an osmolyte that protects the cells against changes in salinity. The results suggest that DMSP is not used as a sole sulfur source in the biosynthesis of TDA, and show that there is a correlation between salinity, DMSP, and the presence of Tda homologs.

The genetic data from the current study, specifically the identification of paaIJK and tdaC (prephenate dehydratase), indicate that TDA biosynthesis originates from the shikimate pathway and proceeds through phenylacetate (FIG. 9). The results also show that phenylacetate-CoA and CoA metabolism is vital to TDA production and are consistent with TdaD-F involvement in a ring expansion reaction that converts PAA-CoA to a seven-member tropolone ring (step 8 in FIG. 9). TdaB, a homolog of glutathione S-transferase, is a potential agent in the addition of sulfur to the nascent TDA molecule.

Accordingly, FIG. 9 provides a putative model of the TDA biosynthetic pathway, based on the findings of the present application. The pathway involves phenylacetate derivation from shikimate-chorismate and degradation pathway providing precursors (step 1~6) and an core oxidative ring-expansion pathway forming the seven carbon tropolone skeleton (step 7~10) followed by sulfur-oxygen exchange (step 11~15), consistent with the proposed TDA synthesis based on chemical labeling studies in *Pseudomonas* CB-104 (Cane, D. E., et al. *J. Am. Chem. Soc.* (1992) 114:8479-8483). The protein assignment was based on predicted functions.

The compounds shown in FIG. 9 include the following:

TABLE 5

| Compound Produced from Reaction: | International Union of Pure and Applied Chemistry (IUPAC) name |
|---|---|
| 6 | 1,2-dihydro-phenylacetyl-CoA |
| 8 | 2-hydroxy-7-oxo-cyclohepta-3,5-dienecarboxylic acid |
| 9 | 2,7-dihydroxy-cyclohepta-1,3,5-trienecarboxylic acid |
| 10 | 2,7-dihydroxy-3-oxo-cyclohepta-1,4,6-trienecarboxylic acid |
| 11 | 2,7-dihydroxy-3-thioxo-cyclohepta-1,4,6-trienecarboxylic acid |
| 13 | 7-hydroxy-2-mercapto-3-thioxo-cyclohepta-1,4,6-trienecarboxylic acid |

Identification of a LysR homolog in TdaA is consistent with the regulation of TDA biosynthesis involving a cofactor. In other bacteria, LysR cofactors can function as precursor molecules required to synthesize the final product, implicating molecules in the shikimate pathway, phenylacetate, or other TDA precursors as being required for maximal expression of the tda genes. Consistent therewith, modifications of the broth by addition of phenylalanine and histidine significantly increase production of TDA from *Phaeobacter* T5.

The present application therefore disclose the genes and proteins required for TDA synthesis by *roseobacters*, and the occurrence of tda genes on a previously unknown megaplasmid (pSTM3) of TM1040, as aspects of the present invention. Sequencing of the 130kb pSTM3 plasmid bearing genes required for TDA synthesis has been carried out with determination of sequences for pSTM3 partial sequence, contiguous tdA~tdaE (SEQ ID NO: 7; FIG. 10), tdaF and membrane protein gene (SEQ ID NO: 8; FIG. 11), lipoprotein (SEQ ID NO: 9), and repC (SEQ ID NO: 10).

Another aspect of the invention relates to a methodology for purification of TDA and intermediate compounds, including the use of solid phase extraction techniques to obtain tropodithietic acid from *Silicibacter* sp. TM1040.

A still further aspect of the invention relates to a method of purification of TDA by HPLC techniques.

An illustrative purification technique is set forth in Example 9 below.

The invention provides an effective and useful biosynthetic capability for the production of tropodithietic acid (TDA) by use of *Roseobacter* bacteria. TDA is a useful sulfur-containing antibiotic compound. The biosynthetic route of the present invention enables scalable production of TDA and TDA derivatives.

The backbone of TDA is a seven member aromatic tropolone ring, which is highly significant as tropolone derivatives, notably hydroxylated forms, are medically important sources of antibacterial, antifungal, antiviral, and antiparasitic agents. Chemical synthesis of tropolone and derivatives can be difficult, making natural sources of tropolone precursors often the preferred choice as starting material for the synthesis of new tropolone antibiotics. The mutants obtained in this study may lead to the development of bacterial sources of medically important tropolone compounds and a suite of new antimicrobial agents based on TDA.

As is demonstrated in Example 10 below, tropodithietic acid identified by the above methods, and exemplified in the Examples set forth below can be utilized in methods of treating or preventing bacterial disease in a subject in need of such treatment or prevention. Antibiotic compositions containing TDA isolated from bacteria of the *Roseobacter* clade can be administered to subjects in need of such an antibacterial composition. Such a subject may have a malady involving bacterial disease or bacterial infection. Administration of the TDA-containing antibacterial composition is effective in treating the bacterial disease or infection, where the disease or infection is caused by any of *Vibrio anguillarium*, *Vibrio cholerae*, *Vibrio coralliilyticus*, *Vibrio shiloi*, *Halomonas* spp., *Mycobacterium marinum*, *Mycobacterium tuberculosis*, *Pseudomonas elongate*, *Spongiobacter nikelotolerans*, and *Staphylococcus aureus* (MRSA). Exemplary efficacy of TDA is shown in Example 10. Inhibition of various bacteria by TDA other than that isolated from bacteria of the *Roseobacter* clade was also previously known (Bruhn, J. B., et al., *Appl Environ Microbiol* (2007) 73: 442-450; Collins, L., et al. *Antimicrob. Agents Chemother.* (1997) 41: 1004-1009.)

The advantages and features of the invention are further illustrated with reference to the following examples, which are not to be construed as in any way limiting the scope of the invention but rather as illustrative of one embodiment of the invention in a specific application thereof.

EXAMPLE 1

Bacteria and Media Preparation

The strains used in this study are listed in (Table 1). *Silicibacter* sp. TM1040, *Phaeobacter* 27-4 and *Vibrio anguillarum* 90-11-287 were grown and maintained in 2216 marine broth or 2216 agar as recommended by the manufacturer (BD Biosciences, Franklin Lakes, N.J.). A marine basal minimal medium (MBM; per liter: 8.47 g Tris HCl, 0.37 g of $NH_4Cl$, 0.0022 g of $K_2HPO_4$, 11.6 g NaCl, 6 g $MgSO_4$, 0.75 g KCl, 1.47 g $CaCl_2.2H_2O$, 2.5 mg FeEDTA; pH 7.6, 1 ml of RPMI-1640 vitamins [Sigma R7256]) was used for determining carbon and sulfur requirements. Sole carbon sources were added at a final concentration of 1 g/l. *Escherichia coli* strains were grown in Luria-Bertani (LB) broth or on LB agar containing 1.5% Bacto Agar (Becton Dickinson, Franklin Lakes, N.J.). As appropriate, kanamycin was used at 120 μg per ml for *Roseobacter* strains and 50 μg per ml for *E. coli*.

TABLE 1

Bacterial strains and plasmids used.

| Strain/plasmid | Genotype/phenotype | Source of reference |
|---|---|---|
| *Escherichia coli* | | |
| DH5α | F⁻ endA1 hsdR17 ($r_K^-$ $m_K^-$) supE44 thi-1 recA1 gyrA96 relA1 Φ80dlacZΔM15 | Sambrook, J., E. F. Fritsch, and T. Maniatis. 1989. Molecular cloning: a laboratory manual., 2nd ed. Cold Spring Harbor Laboratory Press, Cold Spring Harbor, NY. |
| DH5α(λpir) | DH5α transduced with λpir | Hanahan, D. 1983. Studies on transformation of *Escherichia coli* with plasmids. J. Mol. Biol. 166: 557-580; Kolter, R., M. Inuzuka, and D. R. Helinski. 1978. Transcomplementation-dependent replication of a low molecular weight origin fragment from plasmid R6K. Cell 15: 1199-1208. |
| EC100D pir+ | F⁻ mcrA D(mrr-hsdRMS-mcrBC) f80dlacZDM15 DlacX74 recA1 endA1 araD139 D(ara, leu)7697 galU galK l-rpsL nupG pir+(DHFR). | Epicentre ™ |

TABLE 1-continued

Bacterial strains and plasmids used.

| Strain/plasmid | Genotype/phenotype | Source of reference |
| --- | --- | --- |
| | | *Roseobacters* |
| *Silicibacter* sp. TM1040 | Wild type, antibacterial activity | Miller, T. R., and R. Belas. 2004. Dimethylsulfoniopropionate metabolism by *Pfiesteria*-associated *Roseobacter* spp. Appl. Environ. Microbiol. 70: 3383-3391 |
| | | Mutants derived from TM1040 |
| *Silicibacter* sp. TM1040 SM | None pigment and tda spontaneous strain | current study |
| HG1005 | paaK::EZ-Tn5,Kan | " |
| HG1015 | tdaB::EZ-Tn5,Kan | " |
| HG1050 | tdaF::EZ-Tn5,Kan | " |
| HG1056 | paaJ::EZ-Tn5,Kan | " |
| HG1080 | tdaC::EZ-Tn5,Kan | " |
| HG1110 | tdaD::EZ-Tn5,Kan | " |
| HG1213 | malY::EZ-Tn5,Kan | " |
| HG1220 | cysI::EZ-Tn5,Kan | " |
| HG1244 | tdaH::EZ-Tn5,Kan | " |
| HG1265 | tdaE::EZ-Tn5,Kan | " |
| HG1299 | paaI::EZ-Tn5,Kan | " |
| HG1310 | tdaA::EZ-Tn5,Kan | " |
| *Phaeobacter* sp. 27-4 | Wild type, antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Hjelm, M., O. Bergh, A. Riaza, J. Nielsen, J. Melchiorsen, S. Jensen, H. Duncan, P. Ahrens, H. Birkbech, and L. Gram. 2004. Selection and identification of autochthonous potential probiotic bacteria from turbot larvae (*Scophthalmus maximus*) rearing units. Syst. Appl. Microbiol. 27: 360-371. |
| | | Mutants derived from 27-4 |
| JBB1001 | tdaB::EZ-Tn5,Kan | current study |
| JBB1003 | tdbC::EZ-Tn5,Kan | " |
| JBB1005 | traI::EZ-Tn5,Kan | " |
| JBB1006 | clpX::EZ-Tn5,Kan | " |
| JBB1007 | tdbF::EZ-Tn5,Kan | " |
| JBB1009 | tdbA::EZ-Tn5,Kan | " |
| JBB1011 | tdbD::EZ-Tn5,Kan | " |
| JBB1029 | tdbE::EZ-Tn5,Kan | " |
| JBB1030 | tdaA::EZ-Tn5,Kan | " |
| JBB1044 | metF::EZ-Tn5,Kan | " |
| JBB1045 | tdbB::EZ-Tn5,Kan | " |
| | | Other *Roseobacters* |
| *Roseobacter* algicola 51442 | Wild type, none antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Lafay, B., R. Ruimy, C. Rausch de Traubenberg, V. Breittmayer, M. J. Gauthier, and R. Christen. 1995. *Roseobacter algicola* sp. nov., a new marine bacterium isolated from the phycosphere of the toxin-producing dinoflagellate *Prorocentrum lima*. Int. J. Syst. Bacteriol. 45: 290-296. |
| *Roseobacter* denitrificans 33942 | Wild type, none antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Shiba, T. 1991. *Roseobacter litoralis* gen. nov., sp. nov., and *Roseobacter denitrificans* sp. nov., aerobic pink-pigmented bacteria which contain bacteriochlorophyll a. Syst. Appl. Microbiol. 14: 140-145. |
| *Roseobacter* litoralis 49566 | Wild type, none antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Shiba, T. 1991. *Roseobacter litoralis* gen. nov., sp. nov., and *Roseobacter denitrificans* sp. nov., aerobic pink-pigmented bacteria which contain bacteriochlorophyll a. Syst. Appl. Microbiol. 14: 140-145. |
| *Roseobacter* sp. TM1038 | Wild type, antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Miller, T. R., and R. Belas. 2004. Dimethylsulfoniopropionate metabolism by *Pfiesteria*-associated *Roseobacter* spp. Appl. Environ. Microbiol. 70: 3383-3391 |

TABLE 1-continued

Bacterial strains and plasmids used.

| Strain/plasmid | Genotype/phenotype | Source of reference |
|---|---|---|
| *Roseobacter* sp. TM1039 | Wild type, antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Miller, T. R., and R. Belas. 2004. Dimethylsulfoniopropionate metabolism by *Pfiesteria*-associated *Roseobacter* spp. Appl. Environ. Microbiol. 70: 3383-3391 |
| *Roseovarius* sp. ISM | Wild type, antibacterial activity | |
| *Roseovarius* sp. TM1035 | Wild type, antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Miller, T. R., and R. Belas. 2004. Dimethylsulfoniopropionate metabolism by *Pfiesteria*-associated *Roseobacter* spp. Appl. Environ. Microbiol. 70: 3383-3391 |
| *Roseovarius* sp. TM1042 | Wild type, antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Miller, T. R., and R. Belas. 2004. Dimethylsulfoniopropionate metabolism by *Pfiesteria*-associated *Roseobacter* spp. Appl. Environ. Microbiol. 70: 3383-3391 |
| *Silicibacter pomeroyi* DSS-3 | Wild type, antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Gonzalez, J. M., J. S. Covert, W. B. Whitman, J. R. Henriksen, F. Mayer, B. Scharf, R. Schmitt, A. Buchan, J. A. Fuhrman, R. P. Kiene, and M. A. Moran. 2003. *Silicibacter pomeroyi* sp. nov. and *Roseovarius nubinhibens* sp. nov., dimethylsulfoniopropionate-demethylating bacteria from marine environments. Int. J. Syst. Evol. Microbiol. 53: 1261-1269. |
| *Sulfitobacter* sp.1921 | Wild type, none antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450. |
| *Sulfitobacter* sp. EE36 | Wild type, antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Buchan, A., L. S. Collier, E. L. Neidle, and M. A. Moran. 2000. Key aromatic-ring-cleaving enzyme, protocatechuate 3,4-dioxygenase, in the ecologically important marine *roseobacter* lineage. Appl. Environ. Microbiol. 66: 4662-4672. |
| *Sulfitobacter* sp. SE62 | Wild type, none antibacterial activity | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Buchan, A., E. L. Neidle, and M. A. Moran. 2001. Diversity of the ring-cleaving dioxygenase gene pcaH in a salt marsh bacterial community. Appl. Environ. Microbiol. 67: 5801-5809 |
| *Vibrio anguillarum* 90-11-287 | Wild type, serotype 01, susceptible to tropodithietic acid | Bruhn, J. B., L. Gram, and R. Belas. 2007. Production of antibacterial compounds and biofilm formation by *Roseobacter* species are influenced by culture conditions. Appl. Environ. Microbiol. 73: 442-450; Skov, M. N., K. Pedersen, and J. L. Larsen. 1995. Comparison of pulsed-field gel electrophoresis, ribotyping, and plasmid profiling for typing of *Vibrio anguillarum* serovar O1. Appl. Environ. Microbiol. 61: 1540-1545. |
| | | Plasmid |
| pSTM3 | Harboring tda genes | current study |
| pSTM3-1265 | pSTM3 carrying a Tn5 insertion in tdaE, derived from HG1265 | current study |

EXAMPLE 2

Characterization of Antibiotic

Bacterial spent medium was either injected directly (up to 10 µL) or purified by mixed phase anion-exchange reversed phase mini column chromatography on Oasis MAX columns as previously described. Tropodithietic acid was analyzed by reverse phase liquid chromatography (LC) on an Agilent 1100 HPLC system equipped with a diode array detector (DAD). Separation was conducted using a Phenomenex (Torrance, Calif.) Curosil PFP 15 cm, 2 mm, 3 µm column using a water-acetonitrile (ACN) gradient system. Both solvents contained 200 µL/L trifluoroacetic acid, and started 35%

ACN increasing this linear to 60% in 6 min. The wavelength 304±4 nm was used for detection. LC-DAD with online high resolution mass spectrometry (HR-MS) using positive and negative electrospray was used for validation of tropodithietic acid detection as previously described.

EXAMPLE 3

Transponson Mutagenesis and TDA⁻ Screening

Electrocompetent *roseobacter* strains were prepared following the method described by Garg et al. (Garg, B., R. C. Dogra, and P. K. Sharma. 1999. High-efficiency transformation of *Rhizobium leguminosarum* by electroporation. Appl. Environ. Microbiol. 65:2802-2804.) as modified by Miller and Belas. (Miller, T. R., and R. Belas. 2004. Dimethylsulfoniopropionate metabolism by *Pfiesteria*-associated *Roseobacter* spp. Appl. Environ. Microbiol. 70:3383-3391.) Random transposon insertion libraries were constructed in TM1040 and 27-4 using the EZ-Tn5<R6Kγori/KAN-2>Tnp Transposome™ Kit (Epicentre, Madison, Wis.). Strains were spread onto 2216 plates containing kanamycin and incubated for 1 day at 30° C. Individual Kan$^r$ transposon insertion strains were transferred to 7×7-arrays on 2216 marine agar plus kanamycin to facilitate further screening. To screen for loss-of-function, antibiotic-negative (Tda⁻) mutants, a modification of the method described by Bruhn et al. was used. (Bruhn, J. B., K. F. Nielsen, M. Hjelm, M. Hansen, J. Bresciani, S. Schulz, and L. Gram. 2005. Ecology, inhibitory activity, and morphogenesis of a marine antagonistic bacterium belonging to the Roseobacter clade. Appl. Environ. Microbiol. 71:7263-7270.)

Bacteria were replicated, as a 7×7 array, to a lawn of *Vibrio anguillarum* strain 90-11-287, and incubated at 20° C. for 24 h, after which a zone of clearing indicative of antibiotic production was measured and compared to the parental strain (TM1040 or 27-4). For purposes of this study, Tda⁻ is defined as a strain lacking a detectable zone of clearing on *V. anguillarum*. Strains determined to be Tda⁻ by the modified well-diffusion assay were further tested by incubation at 30° C. for 48 h in 2216 marine broth without shaking. Bacteria were removed by filtering through a 0.22 μm MCE membrane (Millex, Millipore, Bedford, Mass.) and the antibacterial activity of the supernatant measured using the *V. anguillarum* well diffusion assay, as described by Bruhn et al.

EXAMPLE 4

Sole Carbon and Sulfur Growth

Bacterial utilization of sole carbon sources was determined by measuring growth in MBM broth that was modified by replacing glycerol with the carbon source to be tested. Carbon compounds tested included amino acids (alanine, arginine, aspartic acid, cysteine, glutamic acid, glycine, histidine, isoleucine, leucine, methionine, phenylalanine, proline, serine, threonine, tryptophan, tyrosine, valine); sugars (arabinose, fructose, galactose, glucose, lactose, maltose, mannose, N-acetylglucosamine, ribose, sucrose, xylose); tricarboxylic acid cycle (TCA) intermediates (citrate, fumurate, succinate); as well as phenylacetic acid and sodium phenylpyruvate.

Sulfur utilization was tested by growth in MBM containing different sulfur sources: DMSP, cysteine, methionine, sodium sulfate, and sodium sulfite.

EXAMPLE 5

Bioinformatics Analysis

Approximately 1 μg of genomic DNA isolated from the candidate mutant was digested with Nco I, self-religated with T4 DNA ligase, and electroporated into DH5α (λpir). Following selection for kanamycin resistance, Kan$^r$ colonies were picked and the plasmid isolated for bidirectional sequencing with transposon-specific primers as recommended by the supplier (Epicentre, Madison, Wis.). Nucleotide sequence thus obtained was analyzed by BLAST analyses using DNA-DNA homology searches against the *Silicibacter* sp. TM1040 genome (Accession numbers: NC_008044, NC_008043, and NC_0080402). The genes identified are listed in Table 2 for TM1040 and Table 3 for 27-4.

TABLE 2

*Silicibacter* sp. TM1040 genes and encoded proteins required for the regulation and synthesis of tropodithietic acid.

| Gene Number | GenBank Accession Number | Gene Designation | Function | Best Hit Ortholog/E score |
|---|---|---|---|---|
| Ring Precursors, Oxidation, and Expansion | | | | |
| TM1040_3728 | CP000376 | paaK | Phenylacetate oxidoreductase | *Roseobacter* sp. MED193 phenylacetic acid degradation oxidoreductase PaaK/8e−161 |
| TM1040_3726 | CP000376 | paaI | Phenylacetate oxygenase | *Roseobacter* sp. MED193 phenylacetic acid degradation protein PaaI/4e−110 |
| TM1040_3727 | CP000376 | paaJ | Phenylacetate oxygenase | *Roseobacter* sp. MED193 phenylacetic acid degradation protein PaaJ/2e−69 |
| EF139203 | EF139203 | tdaD | 4-hydroxybenzoyl-CoA thioesterase | *Paracoccus. denitrificans* PD1222 conserved hypothetical protein/2e−45 |
| EF139204 | EF139204 | tdaE | Acyl-CoA dehydrogenase | *Paracoccus denitrificans* PD1222 acyl-CoA dehydrogenase/9e−120 |
| EF139201 | EF139201 | tdaB | β-etherase, glutathione S transferase | *Paracoccus denitrificans* PD1222 putative β-etherase (β-aryl ether cleaving enzyme) protein/6e−56 |
| EF130202 | EF130202 | tdaC | Prephenate dehydratase | *Paracoccus denitrificans* PD1222 hypothetical protein/2e−45 |

TABLE 2-continued

*Silicibacter* sp. TM1040 genes and encoded proteins required for the regulation and synthesis of tropodithietic acid.

| Gene Number | GenBank Accession Number | Gene Designation | Function | Best Hit Ortholog/E score |
|---|---|---|---|---|
| Sulfur Metabolism and Addition | | | | |
| TM1040_2581 | CP000377 | malY | β-C-S lyase (cystathionase); amino transferase | *Roseobacter* sp. MED193 aminotransferase, classes I and II/0.0 |
| TM1040_0961 | CP000377 | tdaH | Sulfite oxidase domain protein | *Sulfitobacter* sp. NAS-14.1 hypothetical protein/7e−34 |
| TM1040_1758 | CP000377 | cysI | Sulfite reductase | *Roseobacter* sp. MED193 sulfite reductase/0.0 |
| Co-enzyme A Metabolism | | | | |
| EF139205 | EF139205 | tdaF | Phosphopantothenoylcysteine decarboxylase | *Paracoccus denitrificans* PD1222 flavoprotein/2e−55 |
| Regulatory Mechanism | | | | |
| EF139200 | EF139200 | tdaA | LysR substrate binding domain protein | *Paracoccus denitrificans* PD1222 regulatory protein, LysR:LysR, substrate-binding/1e−29 |

TABLE 3

Sole carbon source tested for TM1040 and mutants.

| Gene | Cys | Trp | Phe | Phenylacetic acid | Sodium phenylpyruvate | Sodium phenylbutyrate | 2216 | Other Amino acid |
|---|---|---|---|---|---|---|---|---|
| WT | + | + | + | + | + | + | + | + |
| paaI | + | − | − | − | − | − | + | + |
| paaJ | + | − | − | − | − | − | + | + |
| paaK | + | − | − | − | − | − | + | + |
| tdaA | + | + | + | + | + | + | + | + |
| tdaB | + | + | + | + | + | + | + | + |
| tdaC | + | + | + | + | + | + | + | + |
| tdaD | + | + | + | + | + | + | + | + |
| tdaE | + | + | + | + | + | + | + | + |
| tdaF | + | + | + | + | + | + | + | + |
| cysI | + | − | − | − | − | − | + | − |
| malY | + | + | + | + | + | + | + | + |
| tdaH | + | + | + | + | + | + | + | + |

Signature amino acid domains in the deduced amino acid sequence of the respective ORFs were identified using BLASTP, Pfam, SMART, and the Conserved Domains Database (CDD; hyper text transfer protocol world wide web address ncbi.nlm.nih.gov/Structure/cdd/cdd.shtml). Homologs in *roseobacters* were identified using BLASTP analysis of Roseobase (hyper text transfer protocol world wide web address roseobase.org/) and Gordon and Betty Moore Foundation Marine Microbial Genome databases (hyper text transfer protocol address research.venterinstitute.org/moore/) with respective predicted protein sequence as the query sequence and a maximum E value of 1E-30. Homologs in the Global Ocean Sampling Expedition metagenomic libraries (hyper text transfer protocol address camera.calit2.net/index) were identified by BLASTP analysis using a cutoff E value 1E-20.

EXAMPLE 6

DNA Extraction and Separation

Chromosomal DNA was extracted from bacterial cells by routine methods or by the DNeasy Blood & Tissue Kit (QIAGEN, Valencia, Calif.). Plasmid DNA was prepared by the alkaline lysis method, digested with NcoI (New England Biolabs, Beverly, Mass.), and the resulting restriction fragments were separated by agarose gel electrophoresis in Tris-acetate-EDTA (TAE) buffer.

Pulsed Field Gel Electrophoresis (PFGE) was performed using a CHEF DR-III clamped homogeneous electric field system (Bio-Rad, Richmond, Calif.) with a 1% agarose gel, a 3- to 15-s pulse ramp, an electrophoresis rate of 6.0 V/cm with an included angle of 120° at a constant temperature of 14° C., and a run time of 26 h. Gels were stained with ethidium bromide (EB) and visualized with a Typhoon 9410 (Amersham Biosciences, Piscataway, N.J.)

EXAMPLE 7

PCR Amplification

Multiplex PCR amplification was used to screen for the presence of tda genes in Tda⁻ mutants. A 716-bp sequence internal to tdaE was amplified using primers 5'-CAGAT-GATGGTGCCAAAGGACTAT-3' (SEQ ID NO: 1) and 5'-GGTCAGTTTCTTCTGCACATACTGG-3' (SEQ ID NO: 2), while (in the same reaction), an internal 401-bp fragment of flaA (accession number: CP000377, locus tag: TM1040_2952) was also amplified using primers 5'-TTGCAGTATC-CAATGGTCGTG-3' (SEQ ID NO: 3) and 5'-TGAAT-TGCGTCAGAGTTTGCC-3' (SEQ ID NO: 4) as a control. Standard PCR amplification conditions were 100 µM dNTP each, 0.2 µM of each primer, 1 U Taq DNA polymerase (New England Biolabs, Beverly, Mass.) in 1× reaction buffer (New England BioLabs) with an initial denaturing step at 94° C. for 3 min, followed by 30 cycles of 94° C. for 1 min each, annealing at 55° C. for 30 s, and an elongation at 72° C. for 1 min.

To detect the tdaA-E locus, PCR amplification was conducted with a forward primer complementary to tdaA (5'-CGCTTTCCGGAACTGGAGAT-3' (SEQ ID NO: 5)) and a reverse primer complementary to tdaE (5'-GGCTGCCGTAT-AGTTTCAGCA-3' (SEQ ID NO: 6)) using the Expand Long Template PCR System (Roche Applied Science, Indianapolis, Ind.) and the PCR program conditions and cycle parameters as described by the supplier.

EXAMPLE 8

DNA Hybridization

DNA:DNA hybridization by Southern 'slot' blot (Ausubel, F. M., et al., *Current protocols in molecular biology*. (2001) John Wiley & Sons, Inc., New York, N.Y.) was used to detect the presence of tda genes in other *roseobacters*. The *roseobacter* strains used were: *Phaeobacter* strain 27-4, *Roseobacter algicola* ATCC 51442, *Roseobacter denitrificans* ATCC 33942, *Roseobacter litoralis* ATCC 49566, *Roseobacter* sp. strain TM1038, *Roseobacter* sp. strain TM1039, *Roseovarius* sp. strain TM1035, *Roseovarius* sp. strain TM1042, *Roseovarius* strain ISM, *Silicibacter pomeroyi* DSS-3, *Silicibacter* sp. strain TM1040, *Sulfitobacter* strain EE36, *Sulfitobacter* strain 1921, *Sulfitobacter* strain SE62, and *Vibrio anguillarum* 90-11-287.

Following extraction, 100 ng of total genomic DNA purified from each strain was spotted onto a positively charged nylon membrane (Roche). The DNA was cross-linked to the membrane with ultraviolet light using a Stratalinker UV Crosslinker (Stratagene, La Jolla, Calif.), followed by prehybridization of the membrane at 25° C. for 30 min, using the DIG High Prime DNA Labeling and Detection Starter Kit II (Roche) as described by the manufacturer. The membrane was incubated at 25° C. overnight with a double-stranded DNA probe prepared by Hind III digestion of a plasmid bearing tdaA cloned from strain HG1310 that was labeled with digoxigenin-dUTP using random priming as recommended by the manufactures (Roche). Unbound labeled DNA was removed from the membrane by 2×5 min in 2×SSC, 0.1% SDS followed by 2×15 min in 0.2×SSC, 0.1% SDS (Ausubel, F. M., et al., *Current protocols in molecular biology*. (2001) John Wiley & Sons, Inc., New York, N.Y.). In the southern blot, the membrane was prehybridized for 30 min in the same buffer to which was added a tdaD gene probe, and the probe allowed to hybridize overnight at 42° C. The blots were washed under high stringency conditions following the manufacturer's protocol (Roche applied science) and exposed to Lumi-film chemiluminescent detection film (Roche) for subsequent detection of the hybridization signal.

EXAMPLE 9

Purification of TDA

Purification of Compound.
1. *Roseobacter* 27-4 was grown in 500 ml MB in a 5 liter volumetric flask at 25° C. for 4 days.
2. The cells were removed by centrifugation (10,000×g for 10 min).
3. The pH of the supernatant was adjusted to 3.5
4. Extraction was carried out with 3 times 500 ml ethyl acetate acidified with 0.1% formic acid (FA)
5. The organic phase was transferred to a vessel and evaporated to dryness under nitrogen flow.
6. The dry ethyl acetate extract was redissolved in 3×3 ml acetonitrile (CAN)-water (1:19) containing 1% FA
7. The redissolved extract was sequentially applied to two 60 mg Oasis MAX columns (Waters, Milford, Mass.) which had previously been sequentially conditioned with 4 ml methanol (HPLC grade) and 3 ml CAN-water (1:19) containing 1% FA.
8. After loading the samples by gravity the columns were washed with 4 ml PBS buffer (pH 7).
9. 3.5 ml CAN-water (1:1) was passed through the column and collected (fraction 1)
10. 3.5 ml CAN-water (9:1) (fraction 2)
11. 3.5 ml CAN-water (1:1) with 2% FA (fraction 3)
12. 3.5 ml CAN-water (9:1) with 2% FA (fraction 4)
13. The solvents were then removed in vacuo on a SpeedVac (ThemoSavant, Holbrook, N.Y.).

EXAMPLE 10

Antibiotic Activity of TDA-Containing Composition

Tropodithietic Acid (TDA) Minimal Inhibitory Concentration (MIC) against various types of bacteria was found to be as follows:

Against *Mycobacterium tuberculosis* strain H37Rv
MIC=7.8 ug/ml
Results: TDA kills *M. tuberculosis*
Against Methicillin-resistant *Staphylococcus aureus* (MRSA) strain USA300
MIC=40 ug/ml
Results: TDA kills MRSA
Against *Vibrio anguillarium*
MIC=1.5 ug/ml
Results: Confirms that TDA kills *V. anguillarium* and provides numerical data (See FIG. 12); when exposed to 5 ug TDA per ml (ca. 3× MIC), *V. anguillarium* stopped swimming within 70 sec, suggesting that TDA activity affects either membrane integrity or disrupts proton motive force (membrane potential) of the cells. It is unlikely that the mechanism of action of TDS involves inhibition of protein, DNA or RNA synthesis, transcription, or translation, all of which would require more time to inhibit.

*V. anguillarium* was exposed to 5 ug TDS per ml (3× MIC) for 90 minutes, after which the cells were washed and suspended in fresh nutrient broth. TDA-exposed *V. anguillarium* failed to grow, while the control (cells exposed to buffer) grew normally. The results, as set forth in the graph of FIG. 13 indicate that the activity of TDA is bactericidal for this bacterial species, not simply bacteristatic.

Although the invention has been described with reference to the above examples, it will be understood that modifications and variations are encompassed within the spirit and scope of the invention. Accordingly, the invention is limited only by the following claims.

What is claimed is:

1. An isolated nucleic acid comprising a polynucleotide encoding at least one protein required for regulation and synthesis of tropodithietic acid by *Roseobacter* bacteria and wherein the isolated nucleic acid sequence is either SEQ ID NO:7 or SEQ ID NO:8.

2. An isolated protein comprising a protein encoded by the nucleic acid sequence of either SEQ ID NO:7 or SEQ ID NO:8, wherein the protein is at least one protein required for regulation and synthesis of tropodithietic acid selected from a LysR substrate binding domain protein, a β-etherase, a prephenate dehydratase, a dehydroxybenzoyl-Co A thioesterase, an acyl-CoA dehydrogenase, a phosphopantothenoylcysteine decarboxylase, a membrane protein, and a phosphoesterase of a *Roseobacter* bacteria.

* * * * *